(12) United States Patent
Lee et al.

(10) Patent No.: US 12,295,981 B2
(45) Date of Patent: May 13, 2025

(54) **PHARMACEUTICAL COMPOSITION FOR PREVENTING OR TREATING NEURODEGENERATIVE DISEASES, CONTAINING *ANGELICA GIGAS* NAKAI EXTRACT OR MIXED EXTRACT OF *ANGELICA GIGAS* NAKAI AND BROCCOLI**

(71) Applicant: Astrogenesis Co., Ltd., Seoul (KR)

(72) Inventors: Kang Hyun Lee, Seoul (KR); Min Kuk, Seoul (KR)

(73) Assignee: ASTROGENESIS CO., LTD., Seoul (KR)

( * ) Notice: Subject to any disclaimer, the term of this patent is extended or adjusted under 35 U.S.C. 154(b) by 840 days.

(21) Appl. No.: 17/280,975

(22) PCT Filed: Jul. 2, 2019

(86) PCT No.: PCT/KR2019/008062
§ 371 (c)(1),
(2) Date: Mar. 29, 2021

(87) PCT Pub. No.: WO2020/071620
PCT Pub. Date: Apr. 9, 2020

(65) Prior Publication Data
US 2021/0353698 A1    Nov. 18, 2021

(30) Foreign Application Priority Data
Oct. 1, 2018  (KR) .................. 10-2018-0116945

(51) Int. Cl.
*A61K 36/232*    (2006.01)
*A23L 33/105*    (2016.01)
*A61K 36/31*     (2006.01)
*A61P 25/28*     (2006.01)

(52) U.S. Cl.
CPC .......... *A61K 36/232* (2013.01); *A23L 33/105* (2016.08); *A61K 36/31* (2013.01); *A61P 25/28* (2018.01); *A23V 2002/00* (2013.01)

(58) Field of Classification Search
CPC ...... A61K 36/23; A61K 36/31; A61K 36/232; A23L 33/105
See application file for complete search history.

(56) References Cited

U.S. PATENT DOCUMENTS

| | | | |
|---|---|---|---|
| 2001/0024664 A1* | 9/2001 | Obukowicz | A61P 11/02 424/754 |
| 2011/0003017 A1* | 1/2011 | Park | G01N 33/84 424/725 |
| 2023/0248791 A1* | 8/2023 | Jung | A61K 36/232 424/93.46 |

FOREIGN PATENT DOCUMENTS

| | | |
|---|---|---|
| KR | 10-2009-0112261 | 10/2009 |
| KR | 10-2010-0111786 | 10/2010 |
| KR | 10-2011-0101930 | 9/2011 |
| KR | 10-2012-0037896 | 4/2012 |
| KR | 10-2012-0038372 | 4/2012 |
| KR | 10-2012-0054946 | 5/2012 |
| KR | 10-2015-0044486 | 4/2015 |
| KR | 10-2017-0023512 | 3/2017 |
| KR | 10-1725150 | 4/2017 |
| KR | 20180043251 A * | 4/2018 |
| KR | 10-2018-0091223 | 8/2018 |

OTHER PUBLICATIONS

NCBI taxonomy: *Brassica oleracea* var *italica*, 1 page, https://www.ncbi.nlm.nih.gov/Taxonomy/Browser/wwwtax.cgi?id=36774.*
Lepesant, CR Biologies 338, 2015, 584-592.*
Seon Kyeong Park et al., "Antiamnesic Effect of Broccoli (*Brassica oleracea* var. *italica*) Leaves on Amyloid Beta (Aβ)1-42-Induced Learning and Memory Impairment", Journal of Agricultural and Food Chemistry, 2016, 64(17), pp. 3353-3361, Apr. 14, 2016.
Abhijit Dey et al, "Natural products against Alzheimer's disease: Pharmaco-therapeutics and biotechnological interventions", Biotechnology Advances., GB, (Mar. 1, 2017), vol. 35, No. 2, 178-216, XP055622940, Dec. 30, 2016.
EPO, Extended European Search Report of the corresponding European Patent Application No. 19869912.6., dated May 9, 2022.
KIPO, PCT Search Report & Written Opinion of Application No. PCT/KR2019/008062 dated Oct. 7, 2019.
Kandhasamy Sowndhararajan et al., "Neuroprotective and Cognitive Enhancement Potentials of Angelica gigas Nakai Root: A Review", Scientia Pharmaceutica, 2017, vol. 85, No. 21; doi:10.3390/scipharm85020021, 2017.
Chandini Ravikumar, "Therapeutic Potential of *Brassica oleracea* (Broccoli)—A Review", International Journal of Drug Development and Research, 2015, vol. 7, No. 2, pp. 9-10, Jun. 4, 2015.
SIPO, Office Action of the corresponding CN Patent Application No. 201980079361.0, dated Aug. 13, 2022.
Mahyungfen, "A study on the method of measuring anti-inflammatory antioxidant components and content", Master's thesis in Shenyang University of Pharmacy, May 1, 2009.

* cited by examiner

*Primary Examiner* — Kyle A Purdy
(74) *Attorney, Agent, or Firm* — LEX IP MEISTER, PLLC

(57) ABSTRACT

Provided is a use of an *Angelica gigas* Nakai extract or a mixed extract of *Angelica gigas* Nakai and broccoli for the prevention and/or treatment of neurodegenerative diseases and/or amelioration, the protection of nerve cells and/or the generation of nerve cells.

5 Claims, 11 Drawing Sheets

[FIG. 1]
[FIG. 2]
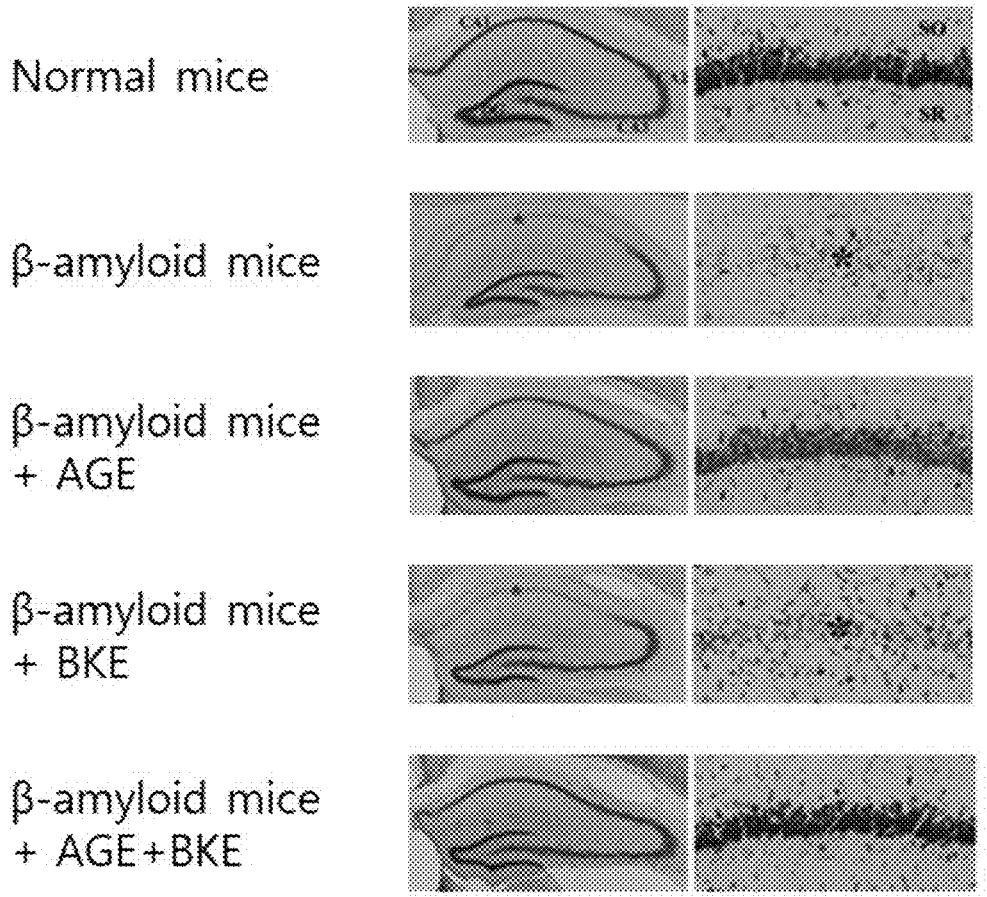

[FIG. 3]
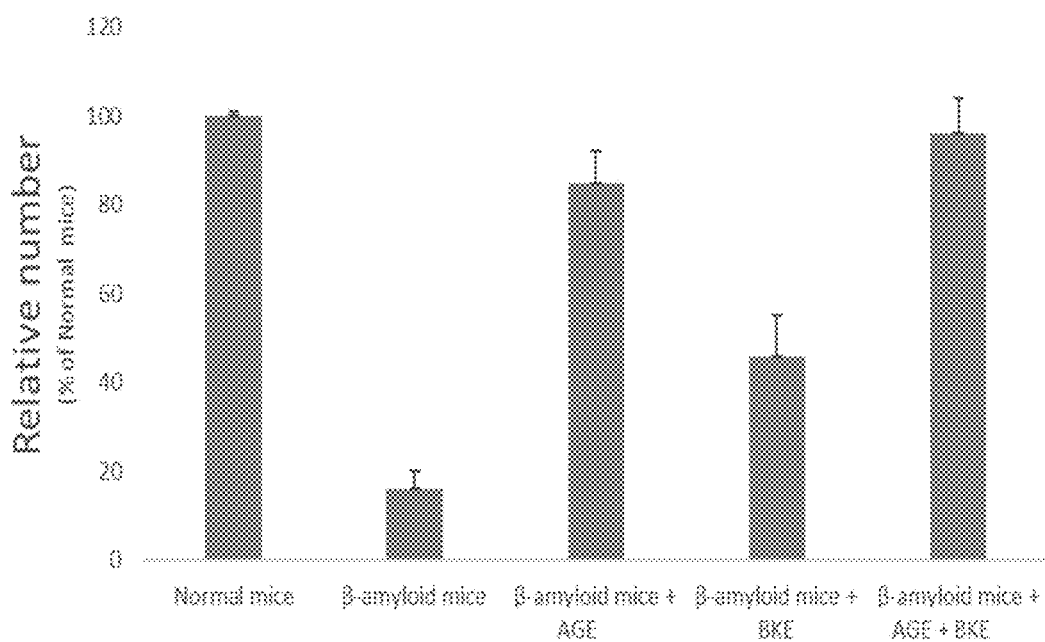
[FIG. 4]
N-Normal mice
T-3X-TG mice
A-3X-TG mice+AGE
B-3X-TG mice+BKE
AB-3X-TG mice+AGE+BKE

[FIG. 5]
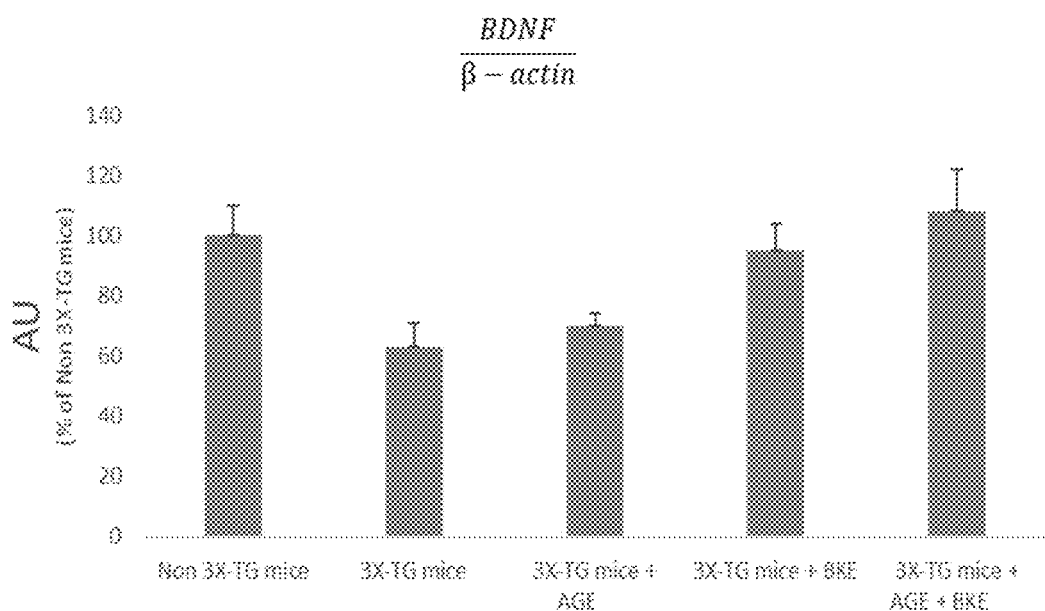
[FIG. 6]
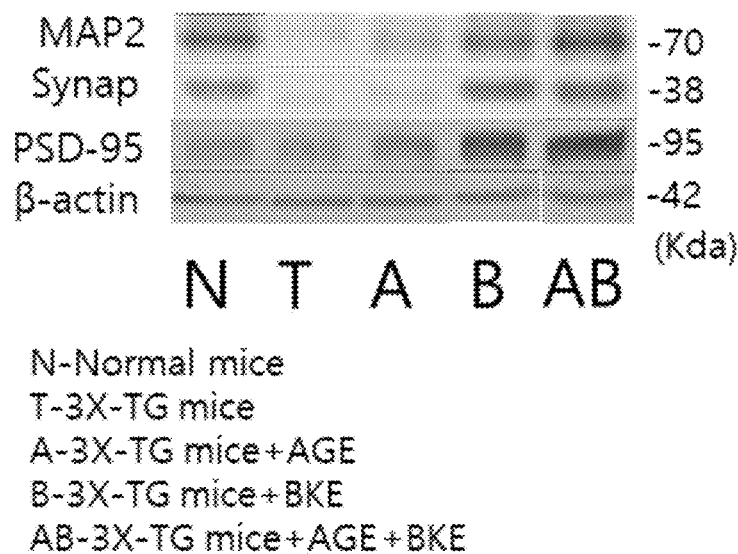
N-Normal mice
T-3X-TG mice
A-3X-TG mice+AGE
B-3X-TG mice+BKE
AB-3X-TG mice+AGE+BKE

[FIG. 7]
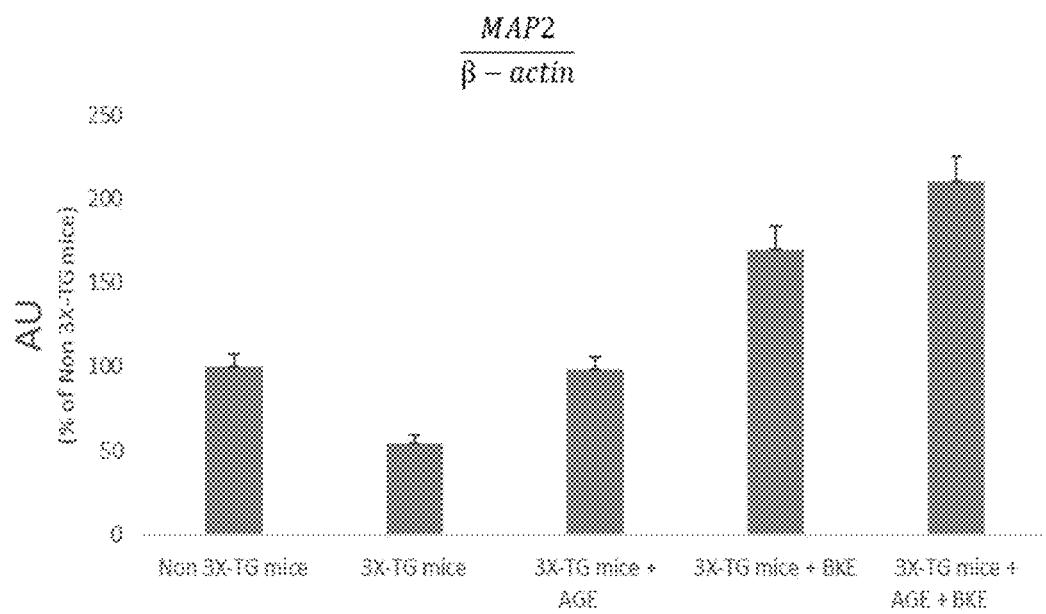
[FIG. 8]
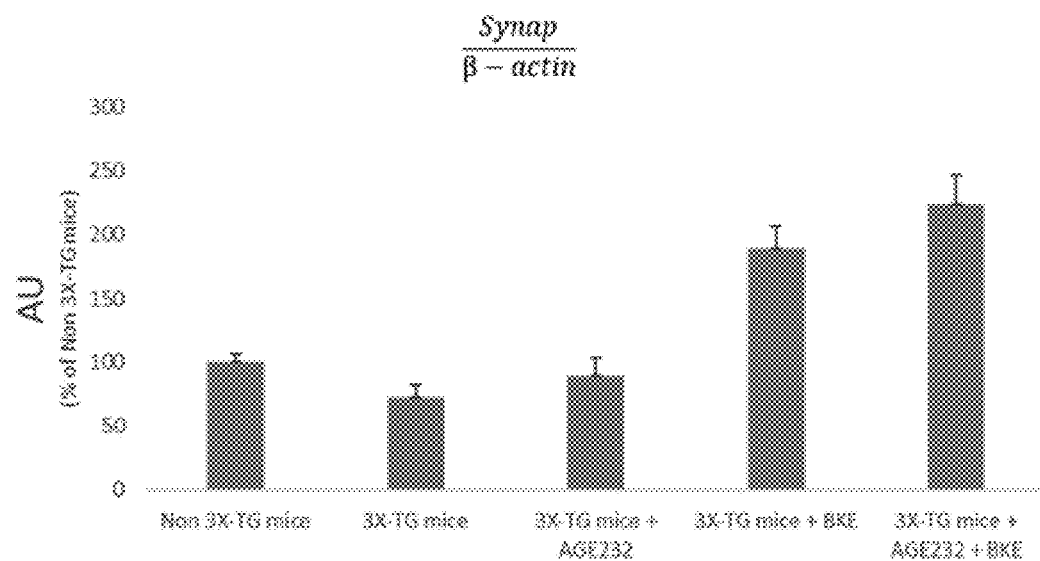

[FIG. 9]
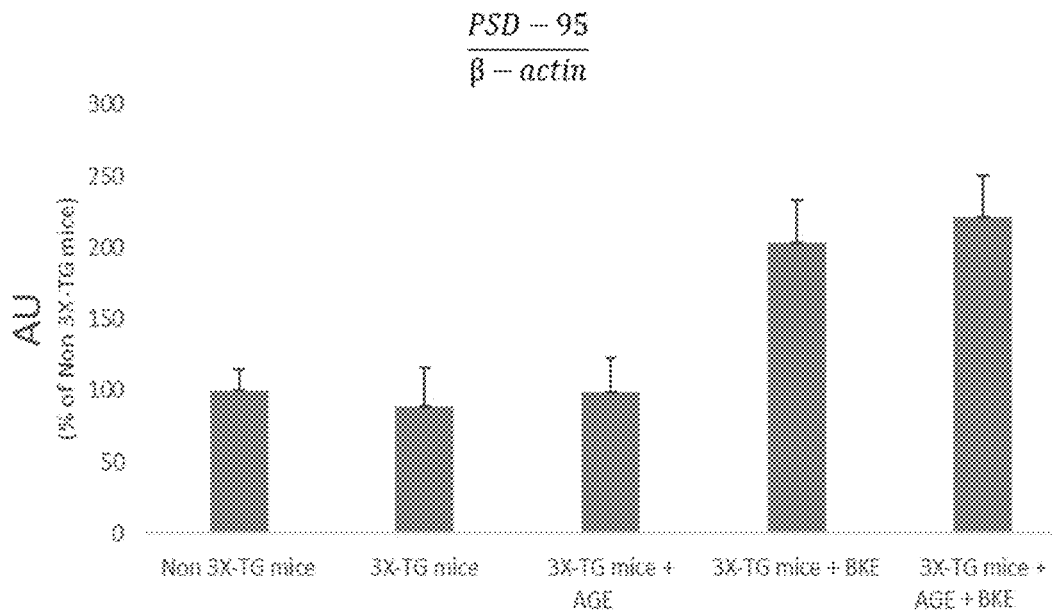
[FIG. 10]
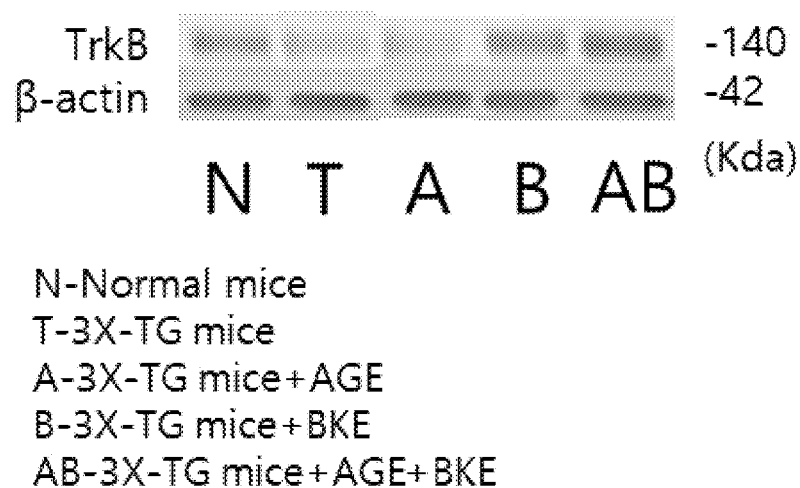
N-Normal mice
T-3X-TG mice
A-3X-TG mice+AGE
B-3X-TG mice+BKE
AB-3X-TG mice+AGE+BKE

[FIG. 11]
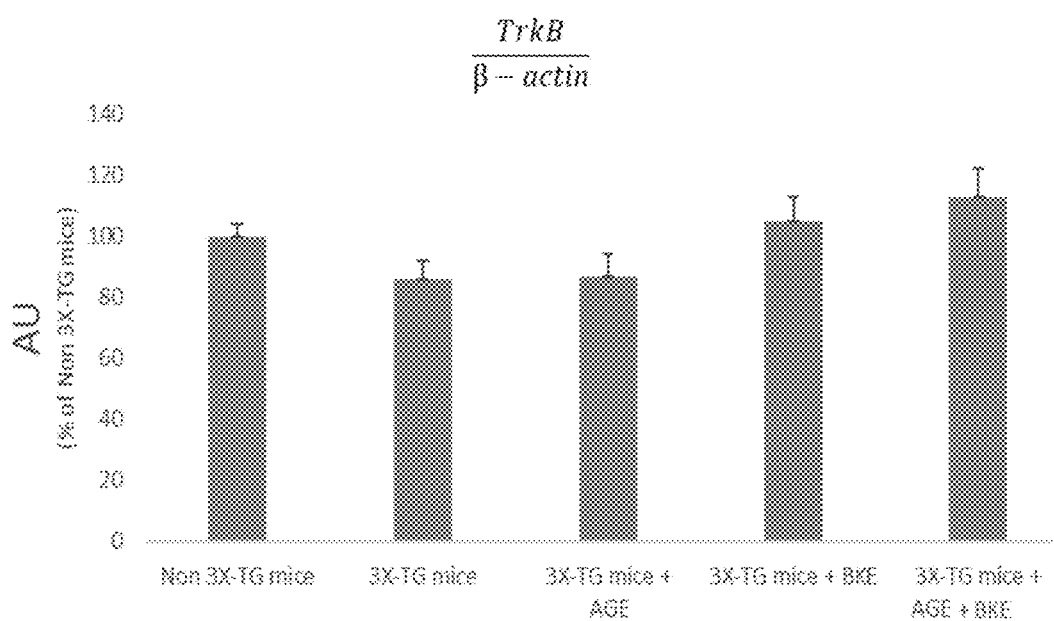

[FIG. 12]
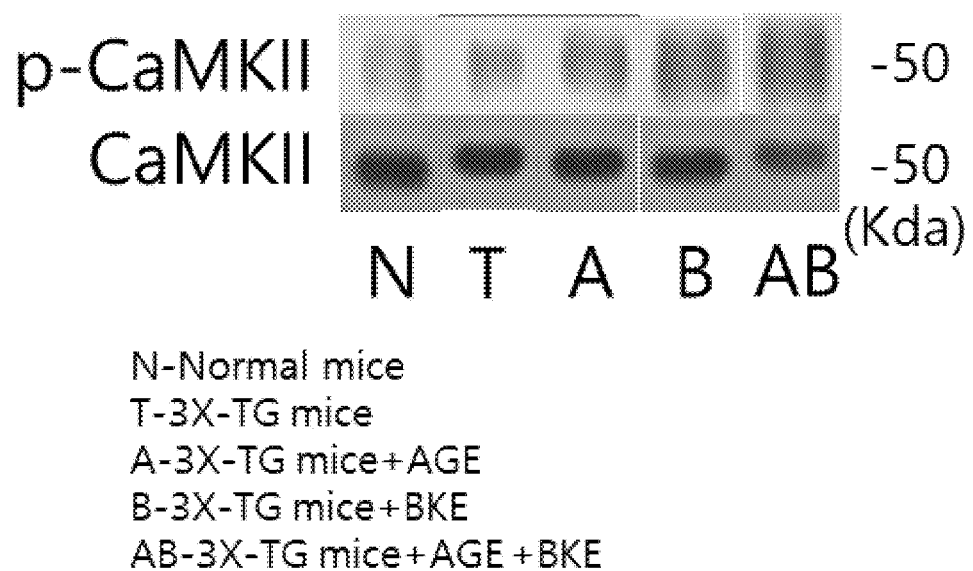
N-Normal mice
T-3X-TG mice
A-3X-TG mice+AGE
B-3X-TG mice+BKE
AB-3X-TG mice+AGE+BKE
[FIG. 13]
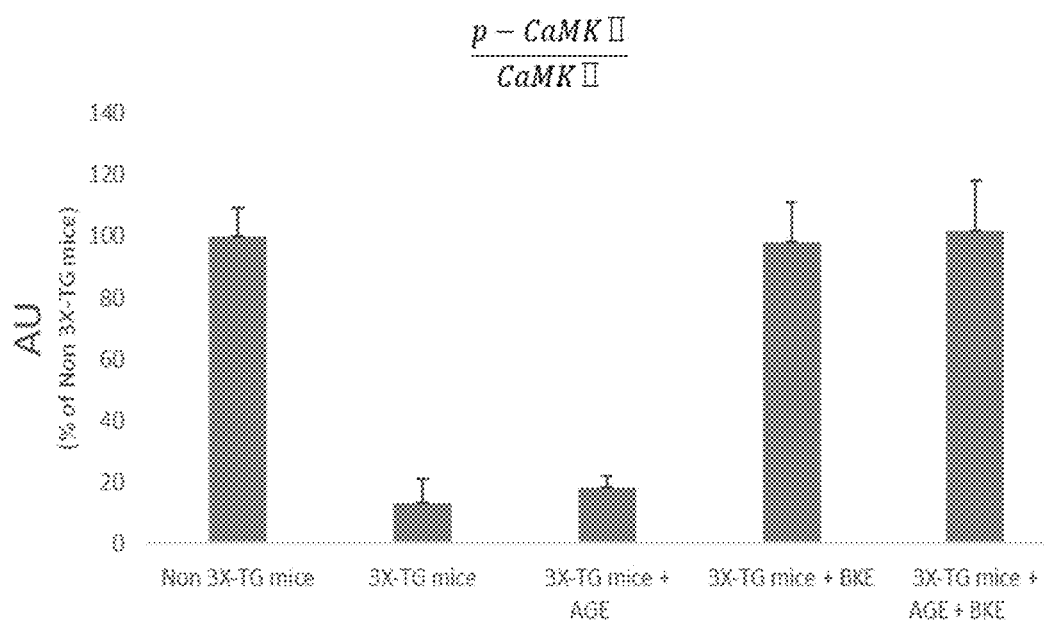

[FIG. 14]
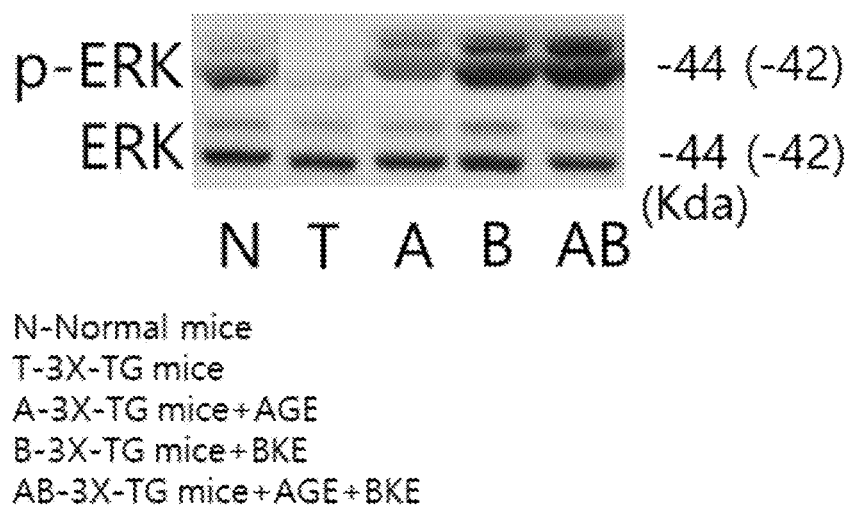
N-Normal mice
T-3X-TG mice
A-3X-TG mice+AGE
B-3X-TG mice+BKE
AB-3X-TG mice+AGE+BKE
[FIG. 15]
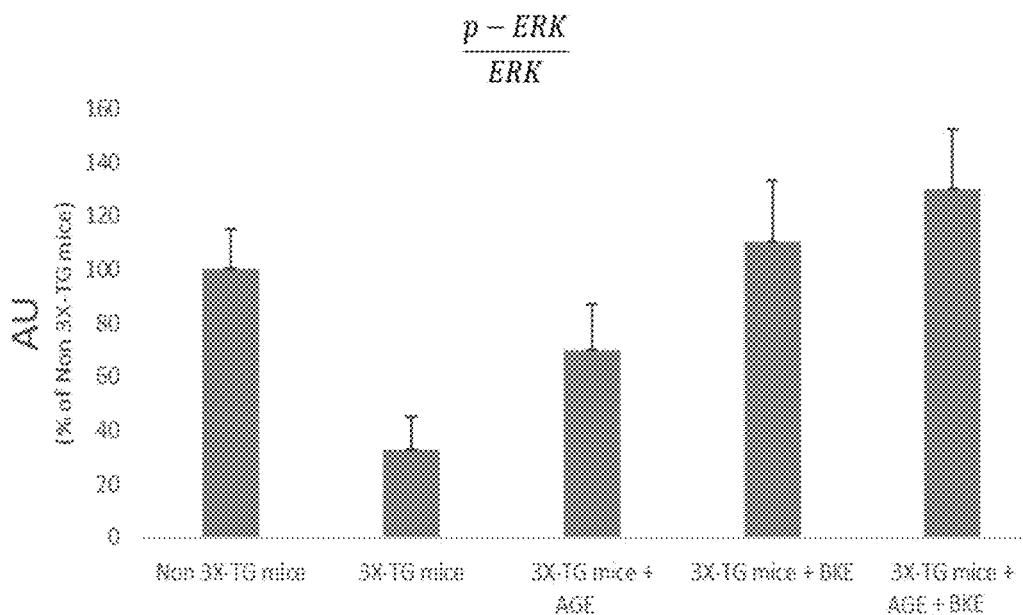

[FIG. 16]
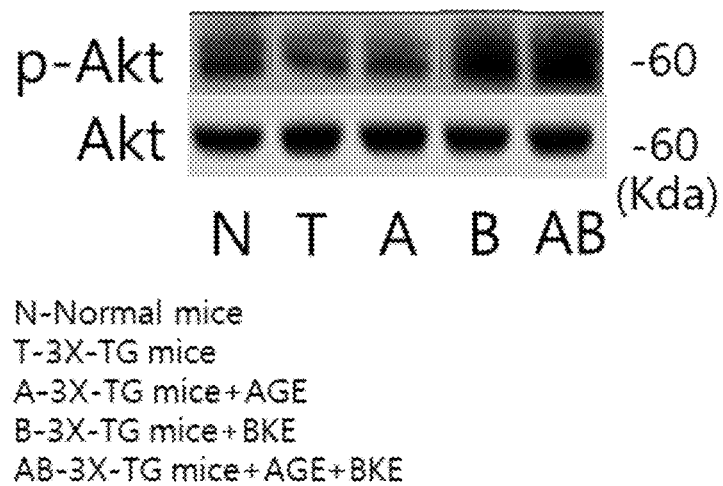
N-Normal mice
T-3X-TG mice
A-3X-TG mice+AGE
B-3X-TG mice+BKE
AB-3X-TG mice+AGE+BKE
[FIG. 17]
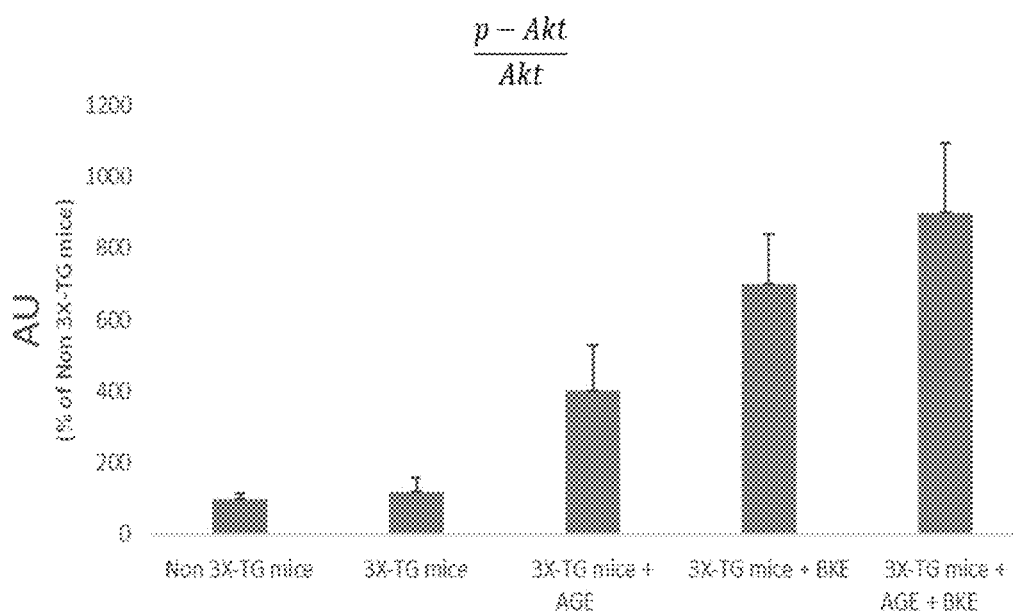

[FIG. 18]
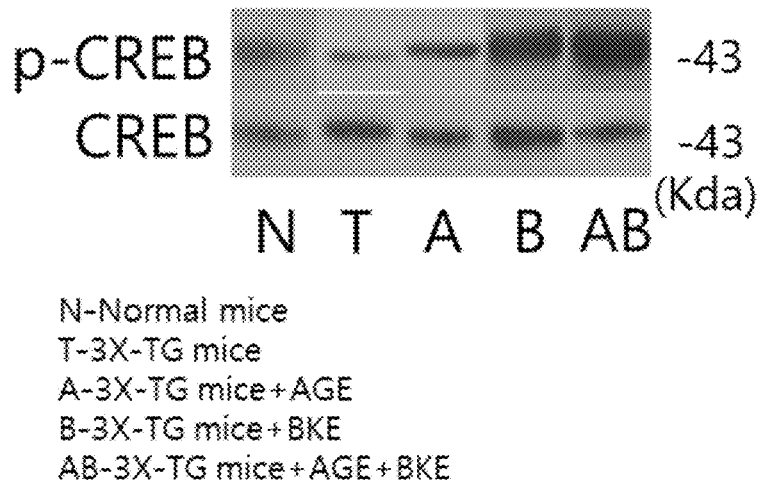
N-Normal mice
T-3X-TG mice
A-3X-TG mice+AGE
B-3X-TG mice+BKE
AB-3X-TG mice+AGE+BKE
[FIG. 19]
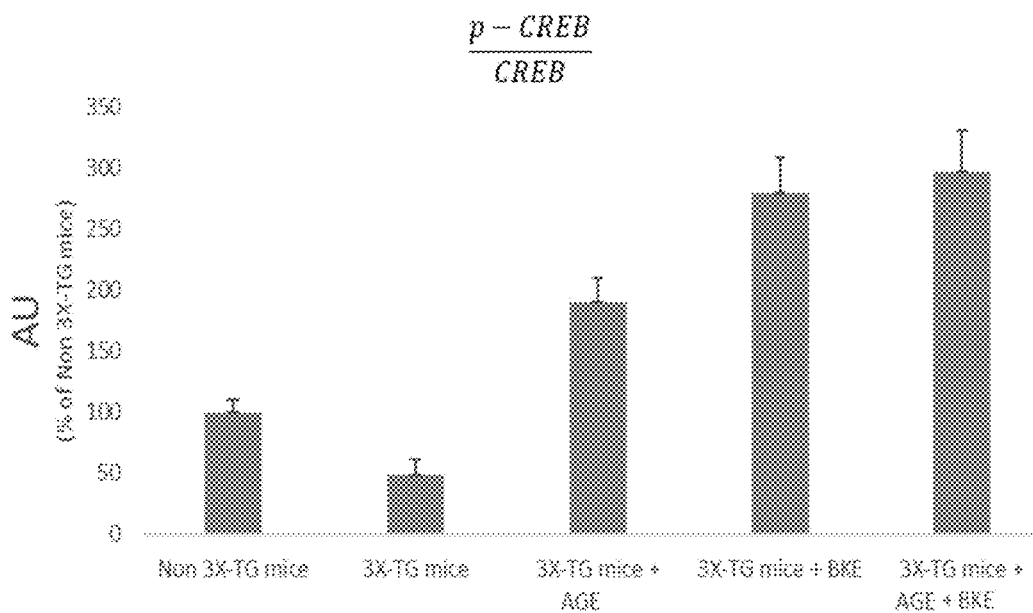

[FIG. 20]
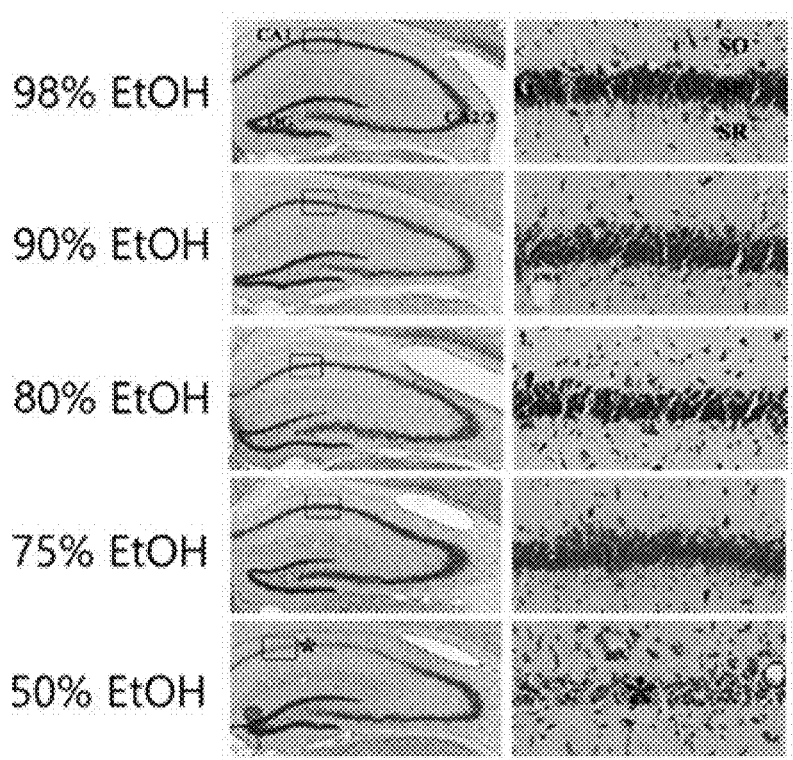
[FIG. 21]
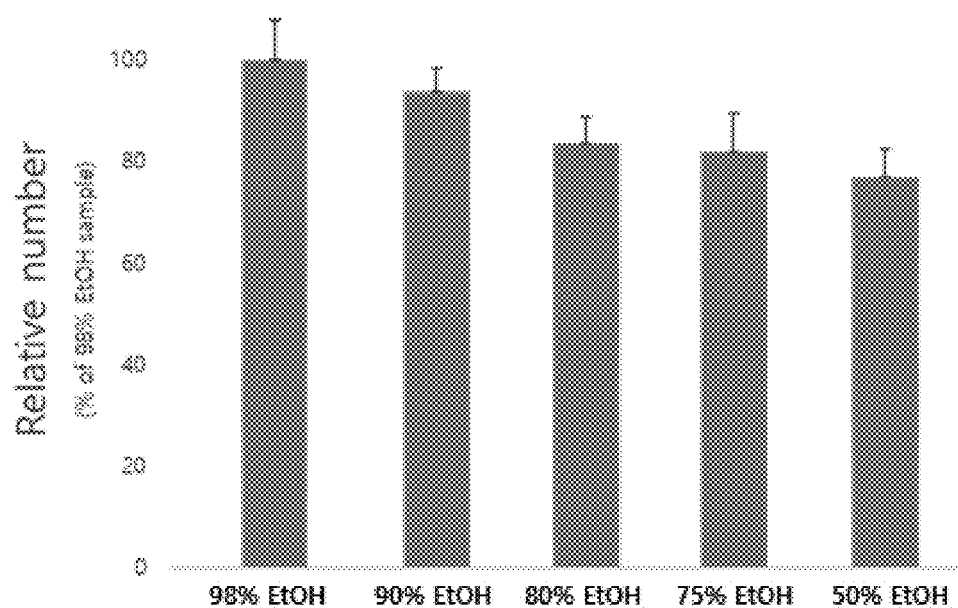

PHARMACEUTICAL COMPOSITION FOR PREVENTING OR TREATING NEURODEGENERATIVE DISEASES, CONTAINING *ANGELICA GIGAS* NAKAI EXTRACT OR MIXED EXTRACT OF *ANGELICA GIGAS* NAKAI AND BROCCOLI

TECHNICAL FIELD

Provided is a pharmaceutical composition for the prevention and/or treatment of neurodegenerative diseases comprising an *Angelica gigas* Nakai extract or a mixed extract of *Angelica gigas* Nakai and broccoli (*Brassica oleracea* var. *italica*), and a pharmaceutical composition for combined administration for preventing and/or treating neurological diseases, comprising an *Angelica gigas* Nakai extract or a mixed extract of *Angelica gigas* Nakai and broccoli.

BACKGROUND ART

With the aging of the population, the prevalence and incidence of degenerative diseases are increasing. In particular, the number of patients with dementia-related diseases is rapidly increasing due to the global aging of the population. According to Alzheimer's Disease International (ADI), there were approximately 44.35 million people worldwide living with dementia in 2013, and the number of people with dementia is estimated to reach 75.62 million in 2030 and 135.46 million in 2050. In the case of Alzheimer's disease, which is the most common of several types of dementia, the pathophysiology is gradually revealed, and many studies have been conducted for the development of therapeutic agents. However, there is no news about the development of an effective therapeutic agents yet.

DETAILED DESCRIPTION OF THE INVENTION

Technical Problem

One embodiment provides a pharmaceutical composition for preventing and/or treating neurodegenerative diseases, a pharmaceutical composition for protecting nerve cells, and/or a pharmaceutical composition for regenerating (or generating) nerve cells, comprising an *Angelica gigas* Nakai extract or a mixed extract of *Angelica gigas* Nakai and broccoli (*Brassica oleracea* var. *italica*) as an active ingredient. Another embodiment provides a method for preventing and/or treating neurodegenerative diseases, a method for protecting nerve cells, and/or a method for regenerating (or generating) nerve cells, the method comprising administering an *Angelica gigas* Nakai extract or a mixed extract of *Angelica gigas* Nakai and broccoli to a subject in need of the prevention and/or treatment of neurodegenerative diseases, the protection of nerve cells, and/or the regeneration (or generation) of nerve cells. The mixed extract of *Angelica gigas* Nakai and broccoli may be a mixture of *Angelica gigas* Nakai extract and broccoli extract, an extract of a mixture of *Angelica gigas* Nakai and broccoli, or a combination thereof.

Another embodiment provides a health functional food for ameliorating neurodegenerative diseases, protecting nerve cells, and/or regenerating (or generating) nerve cells, comprising an *Angelica gigas* Nakai extract or a mixed extract of *Angelica gigas* Nakai and broccoli as an active ingredient. The mixed extract of *Angelica gigas* Nakai and broccoli may be a mixture of *Angelica gigas* Nakai extract and broccoli extract, an extract of a mixture of *Angelica gigas* Nakai and broccoli, or a combination thereof.

Another embodiment provides a method for preparing a composition that has prophylactic, therapeutic and/or ameliorating effects on neurodegenerative diseases, the method comprising preparing an *Angelica gigas* Nakai extract or a mixed extract of *Angelica gigas* Nakai and broccoli.

Yet another embodiment provides a pharmaceutical composition for the combined administration for preventing and/or treating neurodegenerative diseases, protecting nerve cells, and/or regenerating (or generating) nerve cells, comprising an *Angelica gigas* Nakai extract and a broccoli extract. A further embodiment provides a method of preventing and/or treating neurodegenerative diseases, and/or a method of protecting nerve cells, and/or regenerating (or generating) nerve cells, the method including the steps of: administrating an *Angelica gigas* Nakai extract to a subject in need of the prevention and/or treatment of neurological disorders, and administering a broccoli extract to the subject. The step of administrating an *Angelica gigas* Nakai extract and the step of administering a broccoli extract may be performed simultaneously or serially in any order.

Technical Solution

Provided herein is a use of an *Angelica gigas* Nakai extract, or a mixed extract of *Angelica gigas* Nakai and broccoli (*Brassica oleracea* var. *italica*) for preventing and/or treating neurodegenerative diseases.

*Angelica* is a perennial herbaceous plant belonging to the umbel family, and is cultivated mainly for medicinal purposes in Korea, Japan, and China. *Angelica* is divided into *Angelica gigas* Nakai produced in Korea, *Angelica acutiloba* Kitagaw produced in Japan, and *Angelica sinensis* Diels produced in China. It is known that their ingredients and pharmacological effects are different. Since ancient times, *Angelica* has used young sprouts as herbs, and the root is used as a medicine for various diseases such as analgesia, anticancer, reduction of renal toxicity, improvement of liver function, treatment of diabetic hypertension. The *Angelica gigas* Nakai extract used herein may be obtained by extracting the roots of *Angelica gigas* Nakai (e.g., dried and crushed product of the root of *Angelica gigas* Nakai).

Broccoli (*Brassica oleracea* var. *italica*) is an annual dicotyledonous plant belonging to the family mustard of the order papaverales and is widely used for edible purposes. Since broccoli contains more vitamin U than cabbage, it is known to be effective in preventing and treating chronic gastritis, gastric ulcer and the like by strengthening the stomach, and to have excellent anticancer effects on prostate cancer, colon cancer, lung cancer, liver cancer, breast cancer, and pancreatic cancer. The broccoli extract used herein may be obtained by extracting one or more parts selected from the group consisting of seeds, sprouts, flowers, outposts, and the like of Broccoli. The sprout may mean the first stem and/or leaf generated from a seed.

As used herein, the 'treatment' refers to including alleviation or amelioration of symptoms, reduction of the range of diseases, delay or alleviation of the progression of the disease, amelioration, alleviation or stabilization of disease condition or symptoms, partial or complete recovery, prolongation of survival, other beneficial treatment results, and the like. The 'prevention' refers to including all mechanisms and/or effects that act on a subject who does not have a specific disease to prevent the onset of the specific disease or to delay the timing of diseases.

In the present invention, it was confirmed that the *Angelica gigas* Nakai extract, or the mixed extract of *Angelica gigas* Nakai and broccoli shows a protective effect on brain cells against brain nerve damage caused by neurotoxic proteins (see, the effect of protecting brain cells against brain nerve damage caused by beta-amyloid in Example 1), and has a nerve regeneration (e.g., nerve cell generation) effect on an animal model with nerve damage (see, for example, the effect of regenerating (or generating) brain nerve cells in Alzheimer's disease-induced mice in Example 2), thus presenting a neuroprotective effect and/or a nerve cell regeneration (or production) effect of the *Angelica gigas* Nakai extract, or the mixed extract of *Angelica gigas* Nakai and broccoli. The nerve cells may be central nerve cells, for example, brain (nerve) cells.

One embodiment provides a pharmaceutical composition for preventing and/or treating neurodegenerative diseases, a pharmaceutical composition for protecting nerve cells, and/or a pharmaceutical composition for regenerating (or generating) nerve cells, the composition comprising an *Angelica gigas* Nakai extract as an active ingredient. Another embodiment provides a method for preventing and/or treating neurodegenerative diseases, a method for protecting nerve cells, and/or a method for regenerating (or generating) nerve cells, the method comprising administering an *Angelica gigas* Nakai extract to a subject in need of the prevention and/or treatment of neurodegenerative diseases, the protection of nerve cells, and/or the regeneration (or generation) of nerve cells. The nerve cells may be central nerve cells, for example, brain (nerve) cells. The method may further include a step of confirming a subject in need of the prevention and/or treatment of neurodegenerative diseases, the protection of nerve cells, and/or the regeneration (or generation) of nerve cells before the administering step.

Another embodiment provides a pharmaceutical composition for preventing and/or treating neurodegenerative diseases, a pharmaceutical composition for protecting nerve cells, and/or a pharmaceutical composition for the regeneration (or generation) of nerve cells, the composition comprising a mixed extract of *Angelica gigas* Nakai and broccoli as an active ingredient. Another embodiment provides a method for preventing and/or treating neurodegenerative diseases, a method for protecting nerve cells, and/or a method for regenerating (or generating) nerve cells, the method comprising administering a mixed extract of *Angelica gigas* Nakai and broccoli to a subject in need of the prevention and/or treatment of neurodegenerative diseases, protection of nerve cells, and/or regeneration (or generation) of nerve cells. The method may further include the step of identifying a subject in need of the prevention and/or treatment of neurodegenerative diseases, protection of nerve cells, and/or regeneration (or generation) of nerve cells before the administering step. The nerve cells may be central nerve cells, for example, brain (nerve) cells. The mixed extract of *Angelica gigas* Nakai and broccoli may be a mixture of *Angelica gigas* Nakai extract and broccoli extract, or an extract of a mixture of *Angelica gigas* Nakai and broccoli.

Another embodiment provides a pharmaceutical composition for the combined administration for preventing and/or treating neurodegenerative diseases, for protecting nerve cells, and/or for regenerating (or generating) nerve cells, the composition comprising an *Angelica gigas* Nakai extract and a broccoli extract. Another embodiment provides a kit for the combined administration for preventing and/or treating neurodegenerative diseases, for protecting nerve cells, and/or for regenerating (or generating) nerve cells, comprising an *Angelica gigas* Nakai extract and a broccoli extract. The *Angelica gigas* Nakai extract and the broccoli extract contained in the pharmaceutical composition or kit for the combined administration may be in the form of being formulated together (e.g., in the form of a mixture), or may be in the form of being respectively formulated and contained in one dosage unit. Another embodiment provides a method for preventing and/or treating neurodegenerative diseases, a method for protecting nerve cells, and/or a method for regenerating (or generating) nerve cells, the method comprising administering an *Angelica gigas* Nakai extract to a subject in need of the prevention and/or treatment of neurodegenerative diseases, the protection of nerve cells, and/or the regeneration (or generation) of nerve cells. The step of administrating an *Angelica gigas* Nakai extract and the step of administering a broccoli extract may be performed simultaneously or serially in any order.

The *Angelica gigas* Nakai extract may be obtained by extracting an *Angelica gigas* Nakai (e.g., root) with one or more extraction solvents selected from the group consisting of water and a linear or branched alcohol having 1 to 4 carbon atoms. In one embodiment, the *Angelica gigas* Nakai extract may be an *Angelica gigas* Nakai ethanol aqueous solution extract obtained by extracting the *Angelica gigas* Nakai (e.g., root) with 40 to 100% (v/v), 50 to 100% (v/v), 60 to 100% (v/v), 70 to 100% (v/v), 80 to 100% (v/v), 90 to 100% (v/v), 92 to 100% (v/v), 94 to 100% (v/v), 95 to 100% (v/v), 96 to 100% (v/v), 97 to 100% (v/v), or 98 to 100% (v/v) ethanol aqueous solution (e.g., 98% (v/v) aqueous ethanol solution (alcohol)). Further, the *Angelica gigas* Nakai extract may be extracted at a temperature of 10 to 80° C., 10 to 70° C., 10 to 60° C., 10 to 50° C., 20 to 80° C., 20 to 70° C., 20 to 60° C., 20 to 50° C., 30 to 80° C., 30 to 70° C., 30 to 60° C., 30 to 50° C., 40 to 80° C., 40 to 70° C., 40 to 60° C., or 40 to 50° C.

*Angelica gigas* Nakai extract used herein may be those in which, per 100 g, (1) the content of decursin is about 2000 mg or more, about 2200 mg or more, about 2400 mg or more, about 2600 mg or more, about 2800 mg or more, about 2900 mg or more, or about 3000 mg or more, for example, 2000 to 5000 mg, 2000 to 4500 mg, 2000 to 4000 mg, 2000 to 3500 mg, 2200 to 5000 mg, 2200 to 4500 mg, 2200 to 4000 mg, 2200 to 3500 mg, 2400 to 5000 mg, 2400 to 4500 mg, 2400 to 4000 mg, 2400 to 3500 mg, 2600 to 5000 mg, 2600 to 4500 mg, 2600 to 4000 mg, 2600 to 3500 mg, 2800 to 5000 mg, 2800 to 4500 mg, 2800 to 4000 mg, 2800 to 3500 mg, 2900 to 5000 mg, 2900 to 4500 mg, 2900 to 4000 mg, 2900 to 3500 mg, 3000 to 5000 mg, 3000 to 4500 mg, 3000 to 4000 mg, or 3000 to 3500 mg, and/or (2) the content of decursinol angelate is about 1200 mg or more, about 1400 mg or more, about 1600 mg or more, about 1700 mg or more, or about 1800 mg or more, for example, 1200 to 3000 mg, 1200 to 2800 mg, 1200 to 2600 mg, 1200 to 2400 mg, 1200 to 2200 mg, 1400 to 3000 mg, 1400 to 2800 mg, 1400 to 2600 mg, 1400 to 2400 mg, 1400 to 2200 mg, 1600 to 3000 mg, 1600 to 2800 mg, 1600 to 2600 mg, 1600 to 2400 mg, 1600 to 2200 mg, 1700 to 3000 mg, 1700 to 2800 mg, 1700 to 2600 mg, 1700 to 2400 mg, 1700 to 2200 mg, 1800 to 3000 mg, 1800 to 2800 mg, 1800 to 2600 mg, 1800 to 2400 mg, or 1800 to 2200 mg, and/or (3) the content of Nodakenin is about 800 mg or more, about 1000 mg or more, about 1200 mg or more, about 1500 mg or more, about 1700 mg or more, about 2000 mg or more, about 2200 mg or more, about 2400 mg or more, about 2500 mg or more, or about 2600 mg or more, for example, 800 to 5000 mg, 800 to 4500 mg, 800 to 4000 mg, 800 to 3500 mg, 800 to 3200 mg, 1000 to 5000 mg, 1000 to 4500 mg, 1000 to 4000 mg, 1000 to 3500 mg, 1000 to 3200 mg, 1200 to 5000 mg, 1200 to 4500 mg, 1200 to 4000 mg, 1200 to 3500 mg, 1200 to 3200 mg, 1500 to 5000 mg, 1500 to 4500 mg, 1500 to 4000 mg, 1500 to 3500 mg, 1500 to 3200 mg, 1700 to 5000 mg, 1700 to 4500 mg, 1700 to 4000 mg, 1700 to 3500 mg, 1700 to 3200 mg, 2000 to 5000 mg, 2000 to 4500 mg, 2000 to 4000 mg, 2000 to 3500 mg, 2000 to 3200 mg, 2200 to 5000 mg, 2200 to 4500 mg, 2200 to 4000 mg, 2200 to 3500 mg, 2200 to 3200 mg, 2400 to 5000 mg, 2400 to 4500 mg, 2400 to 4000 mg, 2400 to 3500 mg, 2400 to 3200 mg, 2500 to 5000 mg, 2500 to 4500 mg, 2500 to 4000 mg, 2500 to 3500 mg, 2500 to 3200 mg, 2600 to 5000 mg, 2600 to 4500 mg, 2600 to 4000 mg, 2600 to 3500 mg, or 2600 to 3200 mg, and/or (4) the content of beta-sitosterol is 30 mg or more, 50 mg or more, 100 mg or more, 150 mg or more, 200 mg or more, 220 mg or more, 250 mg or more, 270 mg or more, or 300 mg or more, for example, 30 to 1000 mg, 30 to 800 mg, 30 to 600 mg, 30 to 500 mg, 30 to 400 mg, 50 to 1000 mg, 50 to 800 mg, 50 to 600 mg, 50 to 500 mg, 50 to 400 mg, 100 to 1000 mg, 100 to 800 mg, 100 to 600 mg, 100 to 500 mg, 100 to 400 mg, 150 to 1000 mg, 150 to 800 mg, 150 to 600 mg, 150 to 500 mg, 150 to 400 mg, 200 to 1000 mg, 200 to 800 mg, 200 to 600 mg, 200 to 500 mg, 200 to 400 mg, 220 to 1000 mg, 220 to 800 mg, 220 to 600 mg, 220 to 500 mg, 220 to 400 mg, 250 to 1000 mg, 250 to 800 mg, 250 to 600 mg, 250 to 500 mg, 250 to 400 mg, 270 to 1000 mg, 270 to 800 mg, 270 to 600 mg, 270 to 500 mg, 270 to 400 mg, 300 to 1000 mg, 300 to 800 mg, 300 to 600 mg, 300 to 500 mg, or 300 to 400 mg.

The broccoli extract may be obtained by extracting one or more parts selected from the group consisting of seeds, sprouts, flowers, outposts, and the like of broccoli with one or more extraction solvents selected from the group consisting of water and a linear or branched alcohol having 1 to 4 carbon atoms. In one embodiment, the broccoli extract may be a broccoli ethanol aqueous solution extract obtained by extracting the broccoli (e.g., seeds, sprouts, flowers, outposts, and the like) with 20 to 80% (v/v), 30 to 70% (v/v), 40 to 60% (v/v), 45 to 60% (v/v), 48 to 60% (v/v), 40 to 55% (v/v), 45 to 55% (v/v), 48 to 55% (v/v), 40 to 52% (v/v), 45 to 52% (v/v), or 48 to 52% (v/v) ethanol aqueous solution. Further, the broccoli extract may be obtained by adjusting the pH at the time of extraction to, for example, 7 to 9, 7.5 to 9, 7.8 to 9, 7 to 8.5, 7.5 to 8.5, 7.8 to 8.5, 7 to 8.2, 7.5 to 8.2, or 7.8 to 8.2 so as to be advantageous for extracting the content of active ingredients. By extracting broccoli in the above pH range, an extract having a high content of active ingredients in the extract can be obtained. The extraction pH can be adjusted by adding a pH adjuster together with an extraction solvent to extracting broccoli. In one embodiment, the pH adjuster may be one or more selected from the group consisting of sodium hydroxide, calcium hydroxide, potassium hydroxide, etc., without being limited thereto, and can be selected from among all substances whose pH can be adjusted in the above range. In addition, the broccoli extract may be extracted at a temperature of 10 to 80° C., 10 to 70° C., 10 to 60° C., 10 to 50° C., 20 to 80° C., 20 to 70° C., 20 to 60° C., 20 to 50° C., 30 to 80° C., 30 to 70° C., 30 to 60° C., 30 to 50° C., 30 to 45° C., 35 to 60° C., 35 to 50° C., 35 to 45° C., 35 to 60° C., 35 to 50° C., 35 to 45° C., 40 to 80° C., 40 to 70° C., 40 to 60° C., or 40 to 50° C.

The extract of the mixture of *Angelica gigas* Nakai and broccoli may be obtained by extracting a mixture of *Angelica gigas* Nakai (root) and broccoli (seeds, spouts, flowers, outposts, etc.) with one or more extraction solvents selected from the group consisting of water and a linear or branched alcohol having 1 to 4 carbon atoms.

In one embodiment, the mixed extract of *Angelica gigas* Nakai and broccoli may be:

(1) a mixture of (i) 40 to 100% (v/v), 50 to 100% (v/v), 60 to 100% (v/v), 70 to 100% (v/v), 80 to 100% (v/v), 90 to 100% (v/v), 92 to 100% (v/v), 94 to 100% (v/v), 95 to 100% (v/v), 96 to 100% (v/v), 97 to 100% (v/v), or 98 to 100% (v/v) ethanol aqueous solution (e.g., 98% (v/v) ethanol aqueous solution (alcohol)) extract of *Angelica gigas* Nakai (root), and (i) 20 to 80% (v/v), 30 to 70% (v/v), 40 to 60% (v/v), 45 to 60% (v/v), 48 to 60% (v/v), 40 to 55% (v/v), 45 to 55% (v/v), 48 to 55% (v/v), 40 to 52% (v/v), 45 to 52% (v/v), or 48 to 52% (v/v) ethanol aqueous solution (e.g., 50% (v/v) ethanol aqueous solution) extract (optionally, extract extracted under conditions of pH 7 to 9, 7.5 to 9, 7.8 to 9, 7 to 8.5, 7.5 to 8.5, 7.8 to 8.5, 7 to 8.2, 7.5 to 8.2, or 7.8 to 8.2) of broccoli (seeds, spouts, flowers, outposts, etc.), or (2) 40 to 100% (v/v), 45 to 100% (v/v), 48 to 100% (v/v), 50 to 100% (v/v), 60 to 100% (v/v), 70 to 100% (v/v), 80 to 100% (v/v), 90 to 100% (v/v), 92 to 100% (v/v), 94 to 100% (v/v), 95 to 100% (v/v), 96 to 100% (v/v), 97 to 100% (v/v), or 98 to 100% (v/v) ethanol aqueous solution extract of the mixture of *Angelica gigas* Nakai (root) and broccoli (seeds, spouts, flowers, outposts, etc.), or (3) a combination thereof.

Further, the extract or the mixed extract may be those extracted at 10 to 80° C., 10 to 70° C., 10 to 60° C., 10 to 50° C., 20 to 80° C., 20 to 70° C., 20 to 60° C., 20 to 50° C., 30 to 80° C., 30 to 70° C., 30 to 60° C., 30 to 50° C., 40 to 80° C., 40 to 70° C., 40 to 60° C., or 40 to 50° C.

The mixing ratio of *Angelica gigas* Nakai extract and broccoli extract in the mixture of *Angelica gigas* Nakai extract and broccoli extract, or the mixing ratio of *Angelica gigas* Nakai and broccoli in the mixture of *Angelica gigas* Nakai and broccoli may be 1:0.1 to 10, 1:0.1 to 5, 1:0.1 to 4, 1:0.1 to 3, 1:0.1 to 2.5, 1:0.1 to 2.2, 1:0.2 to 10, 1:0.2 to 5, 1:0.2 to 4, 1:0.2 to 3, 1:0.2 to 2.5, 1:0.2 to 2.2, 1:0.5 to 10, 1:0.5 to 5, 1:0.5 to 4, 1:0.5 to 3, 1:0.5 to 2.5, 1:0.5 to 2.2, 1:0.5 to 2, 1:0.7 to 10, 1:0.7 to 5, 1:0.7 to 4, 1:0.7 to 3, 1:0.7 to 2.5, 1:0.7 to 2.2, 1:0.7 to 2, 1:1 to 10, 1:1 to 5, 1:1 to 4, 1:1 to 3, 1:1 to 2.5, 1:1 to 2.2, 1:1 to 2, 1:1.2 to 10, 1:1.2 to 5, 1:1.2 to 4, 1:1.2 to 3, 1:1.2 to 2.5, 1:1.2 to 2.2, 1:1.2 to 2, 1:1.5 to 10, 1:1.5 to 5, 1:1.5 to 4, 1:1.5 to 3, 1:1.5 to 2.5, 1:1.5 to 2.2, 1:1.5 to 2, 1:1.7 to 10, 1:1.7 to 5, 1:1.7 to 4, 1:1.7 to 3, 1:1.7 to 2.5, 1:1.7 to 2.2, or 1:1.7 to 2 (in the above, the weight of *Angelica gigas* Nakai or the solid content weight of *Angelica gigas* Nakai extract: the weight of broccoli or the solid content weight of broccoli extract). The solid content weight refers to the weight of the solids remaining after removing the solvent component of the extract. This is a term used to indicate that the mixing ratio means the ratio between the weights of the active ingredients from which the extraction solvent has been removed so that so that the properties and/or concentration of the extract are not affected, when the mixture is a mixture of *Angelica gigas* Nakai extract and broccoli extract.

The *Angelica gigas* Nakai extract or the mixed extract of *Angelica gigas* Nakai and broccoli contained as an active ingredient in the pharmaceutical composition may be in the form of a dried product, a concentrate, or a concentrated dried product.

The content of the mixed extract of *Angelica gigas* Nakai and broccoli contained as an active ingredient in the pharmaceutical composition can be appropriately adjusted according to the form and purpose of use, the condition of the patient, the type and severity of symptoms, and the like, and the content may be 0.001 to 99.9% by weight, 0.01 to 99.9% by weight, 0.1 to 99.9% by weight, 1 to 99.9% by weight, 10 to 99.9% by weight, 30 to 99.9% by weight, 40 to 99.9% by weight, 50 to 99.9% by weight, 0.001 to 90% by weight, 0.01 to 90% by weight, 0.1 to 90% by weight, 1 to 90% by weight, 10 to 90% by weight, 30 to 90% by weight, 40 to 90% by weight, 50 to 90% by weight, 0.001 to 70% by weight, 0.01 to 70% by weight, 0.1 to 70% by weight, 1 to 70% by weight, 10 to 70% by weight, 30 to 70% by weight, 40 to 70% by weight, 50 to 70% by weight, 0.001 to 50% by weight, 0.01 to 50% by weight, 0.1 to 50% by weight, 1 to 50% by weight, 10 to 50% by weight, 30 to 50% by weight, or 40 to 50% by weight, based on the solid content weight, but is not limited thereto. The solid content weight refers to the weight of the solids from which the solvent component has been removed from the extract, as described above.

As used herein, the neurodegenerative diseases may be selected from among all diseases that show abnormalities in motor regulation ability, cognitive function, perceptual function, sensory function, and autonomic nerve function due to nerve cell death, decrease, function decline, loss of function, or the like. For example, the neurodegenerative diseases may be selected from the group consisting of dementia (e.g., Alzheimer's disease; AD), vascular dementia, mixed dementia, Lewy body dementia, frontotemporal dementia, etc.), Parkinson's disease (PD), Huntington's disease, amyotrophic lateral sclerosis (ALS), and the like.

The subject of administration of the pharmaceutical composition provided herein (e.g., a patient in need of prevention or treatment of neurodegenerative diseases, or a patient in need of protection of nerve cells or regeneration of nerve cells, etc.) may be selected from the group consisting of mammals, including humans, dogs, cats, horses, cows, pigs, goats, rabbits, mice, rats, etc., or cells or tissues isolated therefrom, or cultures thereof, and the like. Further, the pharmaceutical composition may be administered by various routes. The mode of administration may be any mode commonly used in the art, and may be, for example, oral administration, or parenteral administration such as intravenous administration, intramuscular administration, subcutaneous administration, intraperitoneal administration, and local administration of the lesion site (e.g., brain, spinal cord, etc.). The pharmaceutical composition may be used after being formulated into an oral preparation, such as powders, granules, tablets, capsules, suspensions, emulsions, syrups, and aerosols, etc., and a parental preparation, such as epidermal formulations, suppositories, or sterile injection solutions, in accordance with a conventional method.

The pharmaceutical composition may further contain pharmaceutically suitable and physiologically acceptable adjuvants such as carriers, excipients and diluents, etc. in addition to the extract.

Examples of the carriers, excipients and diluents may include lactose, dextrose, sucrose, sorbitol, mannitol, xylitol, erythritol, maltitol, starch, acacia gum, alginate, gelatin, calcium phosphate, calcium silicate, cellulose, methylcellulose, microcrystalline cellulose, polyvinyl pyrrolidone, water, methyl hydroxybenzoate, propyl hydroxybenzoate, talc, magnesium stearate, and mineral oil. When formulated into a preparation, one or more diluting agents or excipients selected from the group consisting of commonly-used fillers, weighting agents, binding agents, wetting agents, disintegrating agents, and surfactants can be used. Solid preparations for oral administration include tablets, pills, powders, granules, capsules, syrups, powdered drugs, and suspensions, and the like, and these solid preparations may be prepared by mixing the extract with at least one excipient, for example, at least one selected from the group consisting of starch, calcium carbonate, sucrose, lactose, gelatin, and the like. In addition to the simple excipient, a lubricant such as magnesium stearate and talc are also used. Liquid preparations for oral administration include at least one selected from the group consisting of a suspension, a liquid for internal use, an emulsion, a syrup, etc. In addition to a commonly used simple diluent such as water and liquid paraffin, various excipients, for example, at least one selected from the group consisting of a humectant, a sweetener, an aromatic, a preservative, etc. may also be contained. Formulations for parenteral administration include a sterilized aqueous solution, a non-aqueous solution, a suspension, an emulsion, a lyophilized formulation and a suppository, transdermal formulations, etc. The non-aqueous solution or suspension may contain at least one selected from the group consisting of propylene glycol, polyethylene glycol, a vegetable oil such as olive oil, an injectable ester such as ethyl oleate, etc.

The pharmaceutical composition may be administered in a pharmaceutically effective amount. A dose of the pharmaceutical composition may be prescribed depending on various factors such as formulation method, administration mode, the patient's age, weight, sex, pathological condition, diet, the time of administration, administration interval, the route of administration, the rate of excretion, and reaction sensitivity. The dose may vary depending on the patient's age, weight, sex, administration mode, health condition, and the severity of diseases. It may be administered once a day or in several divided doses at fixed time intervals according to the decision of a doctor or pharmacist. For example, a singly or daily dose of the pharmaceutical composition may be in the rage of 0.001 to 10000 mg/kg, specifically, 0.01 to 10000 mg/kg, 0.01 to 5000 mg/kg, 0.01 to 3000 mg/kg, 0.01 to 2500 mg/kg, 0.01 to 2000 mg/kg, 0.01 to 1800 mg/kg, 0.1 to 10000 mg/kg, 0.1 to 5000 mg/kg, 0.1 to 3000 mg/kg, 0.1 to 2500 mg/kg, 0.1 to 2000 mg/kg, 0.1 to 1800 mg/kg, 1 to 10000 mg/kg, 1 to 5000 mg/kg, 1 to 3000 mg/kg, 1 to 2500 mg/kg, 1 to 2000 mg/kg, 1 to 1800 mg/kg, 10 to 10000 mg/kg, 10 to 5000 mg/kg, 10 to 3000 mg/kg, 10 to 2500 mg/kg, 10 to 2000 mg/kg, 10 to 1800 mg/kg, 100 to 10000 mg/kg, 100 to 5000 mg/kg, 100 to 3000 mg/kg, 100 to 2500 mg/kg, 100 to 2000 mg/kg, or 100 to 1800 mg/kg, based on the solid content weight of the active ingredient (mixed extract of *Angelica gigas* Nakai and broccoli), but is not limited thereto. The singly or daily dose may be formulated as one formulation into a unit dose form or distributed into separate dose forms, or may be included within a multiple dose package. The above doses illustrate an average case and can be high or low depending on individual differences.

Another embodiment of the present invention provides a method for preparing a composition having an effect of preventing, treating and/or ameliorating neurodegenerative diseases, comprising preparing an *Angelica gigas* Nakai extract, or a mixed extract of *Angelica gigas* Nakai and broccoli.

The step of preparing an *Angelica gigas* Nakai extract may include a step of extracting *Angelica gigas* Nakai (e.g., root) with at least one selected from the group consisting of 1 to 10 times volume, 2 to 8 times volume, or 4 to 6 times volume of water and a linear or branched alcohol having 1 to 4 carbon atoms (e.g., ethanol), for example, 90 to 100% (v/v), 92 to 100% (v/v), 94 to 100% (v/v), 95 to 100% (v/v), 96 to 100% (v/v), 97 to 100% (v/v), or 98 to 100% (v/v) ethanol aqueous solution (e.g., 98% (v/v) ethanol aqueous solution (alcohol)) at 10 to 80° C., 10 to 70° C., 10 to 60° C., 10 to 50° C., 20 to 80° C., 20 to 70° C., 20 to 60° C., 20 to 50° C., 30 to 80° C., 30 to 70° C., 30 to 60° C., 30 to 50° C., 40 to 80° C., 40 to 70° C., 40 to 60° C., or 40 to 50° C.

The step of preparing a mixed extract of *Angelica gigas* Nakai and broccoli may include: 1) mixing *Angelica gigas* Nakai extract and broccoli extract, or 2) extracting a mixture of *Angelica gigas* Nakai and *Brassica oleracea* var with an extraction solvent. For the extraction solvent and extraction temperature used in the extracting step, refer to the previous description of the mixed extract of *Angelica gigas* Nakai and *Brassica oleracea* var.

For example, the step of 1) mixing *Angelica gigas* Nakai extract and broccoli extract may include:

i) extracting *Angelica gigas* Nakai (e.g., root) with at least one selected from the group consisting of 1 to 10 times volume, 2 to 8 times volume, or 4 to 6 times volume of water and a linear or branched alcohol having 1 to 4 carbon atoms (e.g., ethanol), for example, 90 to 100% (v/v), 92 to 100% (v/v), 94 to 100% (v/v), 95 to 100% (v/v), 96 to 100% (v/v), 97 to 100% (v/v), or 98 to 100% (v/v) ethanol aqueous solution (e.g., 98% (v/v) ethanol aqueous solution (alcohol)) at 10 to 80° C., 10 to 70° C., 10 to 60° C., 10 to 50° C., 20 to 80° C., 20 to 70° C., 20 to 60° C., 20 to 50° C., 30 to 80° C., 30 to 70° C., 30 to 60° C., 30 to 50° C., 40 to 80° C., 40 to 70° C., 40 to 60° C., or 40 to 50° C.

ii) extracting broccoli (seeds, spouts, flowers, outposts, etc.) with at least one selected from the group consisting of 1 to 10 times volume, 2 to 8 times volume, or 4 to 6 times volume of water and a linear or branched alcohol having 1 to 4 carbon atoms (e.g., ethanol), for example, 20 to 80% (v/v), 30 to 70% (v/v), 40 to 60% (v/v), 45 to 60% (v/v), 48 to 60% (v/v), 40 to 55% (v/v), 45 to 55% (v/v), 48 to 55% (v/v), 40 to 52% (v/v), 45 to 52% (v/v), or 48 to 52% (v/v) ethanol aqueous solution (e.g., 50% (v/v) ethanol aqueous solution) at 10 to 80° C., 10 to 70° C., 10 to 60° C., 10 to 50° C., 20 to 80° C., 20 to 70° C., 20 to 60° C., 20 to 50° C., 30 to 80° C., 30 to 70° C., 30 to 60° C., 30 to 50° C., 30 to 45° C., 35 to 60° C., 35 to 50° C., 35 to 45° C., 35 to 60° C., 35 to 50° C., or 35 to 45° C., and iii) mixing the *Angelica gigas* Nakai extract extracted in step i) and the broccoli extract extracted in step ii)

The step of ii) preparing broccoli extract may be performed, optionally, by adjusting the pH of the mixture of broccoli and the extraction solvent to 7 to 9, 7.5 to 9, 7.8 to 9, 7 to 8.5, 7.5 to 8.5, 7.8 to 8.5, 7 to 8.2, 7.5 to 8.2, or 7.8 to 8.2, and the pH can be adjusted by adding a conventional pH adjuster. The pH adjuster may include at least one selected from the group consisting of sodium hydroxide, potassium hydroxide, calcium hydroxide, and the like, but is not limited thereto.

The step of preparing an *Angelica gigas* Nakai extract and the step of preparing a broccoli extract may be performed simultaneously or serially in any order.

The step of 2) extracting a mixture of *Angelica gigas* Nakai and broccoli with an extraction solvent may include i') mixing *Angelica gigas* Nakai and broccoli to prepare a mixture, and ii') extracting the mixture with at least one selected from the group consisting of 1 to 10 times volume, 2 to 8 times volume, or 4 to 6 times volume of water and a linear or branched alcohol having 1 to 4 carbon atoms (e.g., ethanol), for example, 40 to 100% (v/v), 45 to 100% (v/v), 48 to 100% (v/v), 50 to 100% (v/v), 60 to 100% (v/v), 70 to 100% (v/v), 80 to 100% (v/v), 90 to 100% (v/v), 92 to 100% (v/v), 94 to 100% (v/v), 95 to 100% (v/v), 96 to 100% (v/v), 97 to 100% (v/v), or 98 to 100% (v/v) ethanol aqueous solution at 10 to 80° C., 10 to 70° C., 10 to 60° C., 10 to 50° C., 20 to 80° C., 20 to 70° C., 20 to 60° C., 20 to 50° C., 30 to 80° C., 30 to 70° C., 30 to 60° C., 30 to 50° C., 40 to 80° C., 40 to 70° C., 40 to 60° C., or 40 to 50° C.

The mixing ratio of the *Angelica gigas* Nakai extract and the broccoli extract or the mixing ratio of *Angelica gigas* Nakai and broccoli are the same as described above.

The extraction time of the extraction step of *Angelica gigas* Nakai extract/broccoli extract is satisfactory as long as the extraction can be performed sufficiently, and may set to the level of 1 hour or more, 2 hours or more, 3 hours or more, or 4 hours or more, for example, 1 to 24 hours, 2 to 24 hours, 3 to 24 hours, 4 to 24 hours, 1 to 12 hours, 2 to 12 hours, 3 to 12 hours, 4 to 12 hours, 1 to 6 hours, 2 to 6 hours, 3 to 6 hours, or 4 to 6 hours, but is not limited thereto.

The extraction process used in the above method can be performed by any commonly used extraction method, and it may be performed, for example, by one or more methods selected from the group consisting of hot water extraction, ultrasonic extraction, reflux extraction, and the like, but is not limited thereto. The method may further include, optionally, drying and/or concentrating the extract by a conventional method, after the extraction process.

Yet another embodiment provides a health functional food for preventing and/or improving neurodegenerative diseases, for protecting nerve cells, and/or for regenerating (or generating) nerve cells, comprising an *Angelica gigas* Nakai extract and a mixed extract of *Angelica gigas* Nakai and broccoli.

The health functional foods are foods produced using raw materials and ingredients (hereinafter, "functional raw materials") having nutrients that are liable to be deficient in daily meals, and functions that are useful to the human body, and means all foods that help to maintain health or prevent and/or ameliorate certain diseases or symptoms, and the form of the final product is not particularly limited. For example, the health functional food may be selected from the group consisting of various foods, beverage compositions, and food additives, but is not limited thereto.

The content of an *Angelica gigas* Nakai extract and a mixed extract of *Angelica gigas* Nakai and broccoli contained in the health functional food is appropriately determined according to the form of the food, the desired use, and the like, and is not particularly limited. For example, the content may be 0.001 to 99% by weight, 0.01 to 99% by weight, 0.01 to 95% by weight, 0.01 to 90% by weight, 0.01 to 80% by weight, 0.01 to 50% by weight, 0.1 to 99% by weight, 0.1 to 95% by weight, 0.1 to 90% by weight, 0.1 to 80% by weight, 0.1 to 50% by weight, 1 to 99% by weight, 1 to 95% by weight, 1 to 90% by weight, 1 to 80% by weight, 1 to 50% by weight, 10 to 99% by weight, 10 to 95% by weight, 10 to 90% by weight, 10 to 80% by weight, 10 to 50% by weight, 25 to 99% by weight, 25 to 95% by weight, 25 to 90% by weight, 25 to 80% by weight, 25 to 50% by weight, 40 to 99% by weight, 40 to 95% by weight, 40 to 90% by weight, 40 to 80% by weight, 40 to 50% by weight, 50 to 99% by weight, 50 to 95% by weight, 50 to 90% by weight, 50 to 80% by weight, 60 to 99% by weight, 60 to 95% by weight, 60 to 90% by weight, or 60 to 80% by weight of the total food weight.

The health functional foods may further include at least one selected from the group consisting of various nutrients, vitamins, minerals (electrolytes), flavoring agents such as synthetic flavors or natural flavors, colorants, enhancers (cheese, chocolate, etc.), pectic acid or salts thereof, alginic acid or salts thereof, organic acids, protective colloidal thickeners, pH regulators, stabilizers, preservatives, glycerin, alcohols, carbonating agents used in carbonated beverages, etc. The ratio of these additives is generally selected from the range of 0.001 to about 20 parts by weight per 100 parts by weight of the total health functional food, but is not limited thereto.

Advantageous Effects

The present invention proposes a neuronal cell protective effect and a neuronal cell regeneration (or generation) effect of an *Angelica gigas* Nakai extract and a mixed extract of *Angelica gigas* Nakai and broccoli, thereby providing new therapies that are highly effective in both the prevention and treatment of neurodegenerative diseases.

BRIEF DESCRIPTION OF THE DRAWINGS

FIG. 1 is a schematic diagram showing the administration schedule of beta-amyloid and the mixed extract for performing a test for confirming the neuroprotective effect of the extract on the induction of nerve damage by beta-amyloid in a mouse model.

FIG. 2 is a photograph showing the results of CV (cresyl violet acetate) staining of the hippocampal tissue of mice to which beta-amyloid was administered after administration of the extract according to one embodiment.

FIG. 3 is a graph showing the results of quantifying the stained hippocampal tissue of FIG. 2.

FIG. 4 shows the result of confirming the expression level of BDNF (brain-derived neurotrophic factor) through Western blotting when the extract according to one embodiment was administered to an Alzheimer's disease mouse model (3×-TG).

FIG. 5 is a graph showing the result of quantifying the expression level of BDNF (BDNF expression level/beta-actin expression level) confirmed by the Western blotting of FIG. 4 using Western blot densitometry analysis.

FIG. 6 shows the result of confirming the expression level of MAP2 (microtubule-associated protein 2), Synap (synaptophysin), and PSD-95 (postsynaptic density protein-95) through Western blotting when the extract according to one embodiment was administered to an Alzheimer's disease mouse model (3×-TG).

FIG. 7 is a graph showing the results of quantifying the expression level of MAP2 (MAP2 expression level/beta-actin expression level) confirmed by the Western blotting of FIG. 6 using Western blot densitometry analysis.

FIG. 8 is a graph showing the results of quantifying the expression level of Synap (Synap expression level/beta-actin expression level) confirmed by Western blotting of FIG. 6 using Western blot densitometry analysis.

FIG. 9 is a graph showing the result of quantifying the expression level of PSD-95 (PSD-95 expression level/beta-actin expression level) by Western blotting of FIG. 6 using Western blot densitometry analysis.

FIG. 10 shows the result of confirming the expression level of TrkB (tyrosine kinase receptor B) through Western blotting when the extract according to one embodiment was administered to an Alzheimer's disease mouse model (3×-TG).

FIG. 11 is a graph showing the results of quantifying the expression level of TrkB (TrkB expression level/beta-actin expression level) confirmed by the Western blotting of FIG. 10 using Western blot densitometry analysis.

FIG. 12 shows the results of confirming the expression level of CAMKII ($Ca^{2+}$/calmodulin-dependent protein kinase II) through Western blotting when the extract according to one embodiment was administered to an Alzheimer's disease mouse model (3×-TG).

FIG. 13 is a graph showing the result of quantifying the expression level of phosphorylated CAMKII (phosphorylated CAMKII expression level/non-phosphorylated CAMKII expression level) confirmed by Western blotting of FIG. 12 using Western blot densitometry analysis.

FIG. 14 shows the result of confirming the expression level of ERK (extracellular signal-regulated kinase) through Western blotting when the extract according to one embodiment was administered to an Alzheimer's disease mouse model (3×-TG).

FIG. 15 is a graph showing the results of quantifying the expression level of phosphorylated ERK (phosphorylated ERK expression level/non-phosphorylated ERK expression level) confirmed by Western blotting of FIG. 14 using Western blot densitometry analysis.

FIG. 16 shows the results of confirming the expression level of Akt (RAC-alpha serine/threonine-protein kinase) through Western blotting when the extract according to an embodiment was administered to an Alzheimer's disease mouse model (3×-TG).

FIG. 17 is a graph showing the results of quantifying the expression level of phosphorylated Akt (phosphorylated Akt expression level/non-phosphorylated Akt expression level) confirmed by the Western blotting of FIG. 16 using Western blot densitometry analysis.

FIG. 18 shows the result of confirming the expression level of CREB (cAMP-responsive element-binding protein) through Western blotting when the extract according to one embodiment was administered to an Alzheimer's disease mouse model (3×-TG).

FIG. 19 is a graph showing the results of quantifying the expression level of phosphorylated CREB (phosphorylated CREB expression level/non-phosphorylated CREB expression level) confirmed by Western blotting of FIG. 18 using Western blot densitometry analysis.

FIG. 20 is a photograph showing the results of CV (cresyl violet acetate) staining of the hippocampal tissue of a mouse to which beta-amyloid was administered after administration of an extract extracted with various concentrations of the extraction solvent.

FIG. 21 is a graph showing the results of quantifying the hippocampal tissue stained in FIG. 20.

DETAILED DESCRIPTION OF THE EMBODIMENTS

Hereinafter, the present invention will be described with reference to examples. However, these examples are for illustrative purposes only, and the scope of the present invention is not limited thereto. It will be obvious to those skilled in the art that the examples described below may be modified without departing from the scope of the essential gist of the present invention.

Example 1: Preparation of Extract 1.1: Preparation of *Angelica gigas* Nakai Extract
1.1.1. Preparation of 98% Ethanol Extract
*Angelica gigas* Nakai roots were washed with clean water and dried sufficiently. The dried *Angelica gigas* Nakai roots were crushed, 5 volume times (500 ml) of ethanol (98% (v/v) ethanol (alcohol)) was added to 100 g of the obtained powder, extracted at 40 to 60° C. for 4 hours or more, and then filtered through a 1 um (micrometer) filter, and the filtrate was heated and concentrated until it became 10 wt.

% of the original weight. Crystalline cellulose was gradually added to the obtained concentrate, continuously concentrated, dried completely, and then powdered to prepare an *Angelica gigas* Nakai ethanol extract powder (hereinafter, referred to as AGE).

1.1.2. Preparation of 90% Ethanol Extract

*Angelica gigas* Nakai roots were washed with clean water and dried sufficiently. The dried *Angelica gigas* Nakai roots were crushed, 5 volume times (500 ml) of ethanol (90% (v/v)) was added to 100 g of the obtained powder, extracted at about 4060° C. for 4 hours or more, and then filtered through a 1 um (micrometer) filter, and the filtrate was heated and concentrated until it became 10 wt. % of the original weight. Crystalline cellulose was gradually added to the obtained concentrate, continuously concentrated, dried completely, and then powdered to prepare an *Angelica gigas* Nakai ethanol extract powder.

1.2: Preparation of Broccoli Extract

The outpost of *Brassica oleracea* var. *italica* was washed with clean water and dried sufficiently. The dried *Brassica oleracea* var. *italica* was crushed, 5 volume times (500 ml) of ethanol (50% (v/v)) was added to 100 g of the obtained powder, and NaOH was added until the pH reached 8. Thereafter, the mixture was extracted three times at 40° C. for 3 hours or more, and then filtered through a 1 um (micrometer) filter, and the filtrate was heated and concentrated until it became 10 wt. % of the original weight. The obtained concentrate was continuously concentrated, dried completely, and then powdered to prepare a *Brassica oleracea* var. *italica* ethanol extract powder (hereinafter, referred to as BKE).

1.3. Preparation of Test Animals

All animals used in the test (ICR mice and 3×-TG mice) were reared under the conditions of a constant light and dark cycle adding light by each 12 hours from 7 am to 7 pm, a temperature of 22° C. to 25° C., and a humidity of 60%. Water and food were freely ingested, and a general pellet-dried feed was used.

Example 2: Neuroprotective Activity Test

Beta-amyloid 1-42 (American Peptide, USA) and beta-amyloid 42-1 (Bachem, Switzerland) were dissolved at a concentration of 37 µl/µl in sterilized 0.1 M phosphate-buffered saline (pH 7.4), and stored until before using the preparative solution. On the other hand, 200 mg/kg of *Angelica gigas* Nakai ethanol extract (AGE) prepared in Example 1.1.1, 400 mg/kg of *Brassica oleracea* var. *italica* ethanol extract (BKE) prepared in Example 1.2, or a mixture of 200 mg/kg of the *Angelica gigas* Nakai ethanol extract (AGE) and 400 mg/kg of the *Brassica oleracea* var. *italica* ethanol extract were dissolved in 10 ml of distilled water, and then administered to the normal mice prepared in Example 1.3 (ICR mice; body weight 18-26 g, 5 mice per group) once daily for 4 weeks. For comparison, a group in which distilled water was administered in an amount of 10 ml instead of the above extract was prepared as a control group. In the bregma of mice to which the extract was administered for 4 weeks, injection was performed at a depth of 2.4 mm using a 50 µl Hamilton microsyringe equipped with a 26-gauge needle, and the above prepared beta-amyloid 1-42 and beta-amyloid 42-1 were each administered in an amount of 5 For the bregma of mice to which the above extract was administered for 4 weeks, injection was injected at a depth of 2.4 mm using a 50 µl Hamilton microsyringe equipped with a 26-gauge needle, and the prepared beta-amyloid $_{1-42}$ and beta-amyloid $_{42-1}$ were respectively administered in an amount of 5 The process of the test is schematically shown in FIG. 1.

For the mouse to which the extract was administered for 4 weeks (28 days) and beta-amyloid was administered as described above, on the third day after administration of beta-amyloid, the experimental animals were subjected to general anesthesia using a gas in which 3% (v/v) isoflurane (Baxtor, USA) was mixed with a mixed gas of nitrogen and oxygen in a ratio of 7:3. While maintaining the anesthetized condition of the experimental animal by using a gas in which 2.5% (v/v) isoflurane was mixed with a mixed gas of nitrogen and oxygen, surgery was performed on the experimental animals Thiophental sodium (Yanhan Corporation, Korea) was injected intraperitoneally at a dose of 30 mg each per 1 kg of body weight, anesthetized, and then a physiological saline (4° C.) containing 1,000 IU of heparin per 1,000 ml was injected into the left ventricle, and washed by perfusion. The perfused and washed animal was subjected to a perfusion fixation using 4% (w/v) paraformaldehyde (4° C.) in 0.1 M phosphate buffer; PB), pH 7.4).

The bone space of the head of the experimental animal for which perfusion fixation was completed was opened using a bone cutter, and the brain was removed. The removed brain of the experimental animals were then post fixed in a 4% paraformaldehyde (0.1 M phosphate buffer (PB), pH 7.4) solution (4° C.) for 4 hours using a stirrer at room temperature. The post fixed brain was placed in a 30% (w/v) sucrose solution (in 0.1 M phosphate buffer) and allowed to settle until it sinks on the bottom. Then, the brain tissue was cut to a thickness of 30 µm with a sliding microtome (Reichert-Jung, Germany) to make a tissue section. The tissue section was placed in a 6 well plate containing a storage solution and stored at 4° C. until staining was performed.

The tissue in which the hippocampal formation was well made in the prepared tissue section was selected. In order to eliminate the preservative solution adhering to the tissue section, the tissue was washed 3 times with 0.01M PBS (pH 7.4) by each 10 minutes. The washed tissue section was smeared on a gelatin-coated slide glass and sufficiently dried at 37° C. The tissue sections were immersed in distilled water for a while, and then immersed in a 2% (w/v) cresyl violet acetate (Sigma, USA) solution for 1 minute, and the tissue section was stained. Subsequently, the stained tissue section was sufficiently washed with running water to remove excess dye adhering to the slide, immersed in distilled water for a while, and then treated sequentially with 50% (v/v), 70% (v/v), 80% (v/v), 90% (v/v), 95% (v/v), and 100% (v/v) ethanol solutions, and dehydration and excess crease violet washing were performed. After confirming that the Nissl body was visible in the tissue section, it was immersed in xylene (Junsey, Japan) to make it transparent, and then encapsulated in Canada balsam (Kanto, Japan).

The respective tissues of the normal group (ICR mice; beta-amyloid-untreated), the control group (extract-untreated and beta-amyloid-treated) and the experimental group (extract-treated and beta-amyloid-treated) were enlarged 40 times the entire hippocampal region and 20 times the CA1 region with an Axio M1 microscope equipped with a digital camera (Axiocam, Cal Zeiss, Germany), and the respective tissue sections were photographed. The photographs of the entire hippocampal region are shown in FIG. 2. Further, after staining the hippocampal region measured in FIG. 2, the result of quantification using a microscope is shown in FIG. 3 as a relative value to the control group.

As shown in FIGS. 2 and 3, it was confirmed that the protective effect of the hippocampus region in the group treated with beta-amyloid after treatment with the extract was excellent as compared with the control group (extract-untreated and beta-amyloid-treated). In particular, in the group treated with *Angelica gigas* Nakai extract (AGE) and the group treated with *Angelica gigas* Nakai extract (AGE) and *Brassica oleracea* var. *italica* extract (BKE) together, an excellent hippocampal area protective effect similar to that of the normal group was observed. These results show that the *Angelica gigas* Nakai extract and the mixed extract of *Angelica gigas* Nakai and *Brassica oleracea* var. *italica* have a neuroprotective effect against nerve damage caused by neurotoxic substances. Furthermore, it shows that it has a preventive effect on neurodegenerative diseases caused by the neurotoxic substances.

Example 3: Nerve Regeneration Activity Test

Mice in which Alzheimer's disease was induced through genetic manipulation (3×Tg-AD, triple-transgenic mouse model of AD, 12 months old, hereinafter "3×-TG mice"; THE JACKSON LABORATORY (USA); female, 4 mice per group, weight about 40 g) was purchased and used. These mice gradually expressed Plaques and tangles, and showed deficiencies in learning ability and memory.

The prepared 12-month-old 3×-TG mice were orally administered for 6 weeks, wherein 200 mg/kg of *Angelica gigas* Nakai ethanol extract (AGE) prepared in Example 1.1.1 and/or 400 mg/kg of *Brassica oleracea* var. *italica* ethanol extract (BKE) prepared in Example 1.2 were dissolved in 10 ml of distilled water and administered alone or in combination 6 times a week for 6 weeks. For comparison, a group to which 10 ml of distilled water was administered instead of the extract was prepared as a control group. The same test was performed using B6129SF2/J mice (female; 4 mice, weight 40 g; THE JACKSON LABORATORY (USA)) as a normal group.

For immunohistochemical analysis, the mouse to which the extract was administered for 6 weeks was anesthetized, and subjected to intracardiac perfusion with 0.01M PBS and 4% (w/v) paraformaldehyde (PFA). Brain was removed and post fixed in 4% (w/v) PFA for 2 days, and cryopreserved in PBS containing 30% (w/v) sucrose for 2 days. Then, it was frozen on powdered dry ice and stored at −80° C. until use. Thereafter, changes in biomarkers related to nerve regeneration were confirmed by Western blot analysis as follows.

Specifically, the Western blot analysis was performed as follows:

The frozen and prepared brain tissues and cells were homogenized in a radioimmunoprecipitation analysis buffer (cell Signaling Technology, Beverly, MIA, USA), and the protein analysis reagents (Bio-Rad, Hercules, CA, USA) were used to measure the concentration of biomarker proteins that could confirm the production of brain (nerve) cells. Protein was separated by electrophoresis on 10% (w/v) sodium dodecyl sulfate polyacrylamide gel, and electrophoretically transferred to a polyvinylidene fluoride membrane (Millipore, Billerica, MA, USA). The membrane was blocked with 5% (v/v) non-fat dry milk or 5% (v/v) PBS, and cultured with a primary antibody against biomarkers such as beta-actin. After incubation with Horseradish-peroxidase-conjugated secondary antibody, the protein band was measured using an enhanced chemiluminescence detection kit (GE Healthcare, St. Giles, UK). The obtained results were quantified using ImageJ software (National Institutes of Health, Bethesda, MD, USA).

The biomarker proteins used in this Example and antibodies thereto are summarized in Table 1 below:

TABLE 1

| Biomarker | Source of primary antibody | Secondary antibody |
|---|---|---|
| BDNF (brain-derived neurotrophic factor) | Santa Cruz | Horseradish-peroxidase-conjugated antibody (Sigma Aldrich) |
| MAP2 (microtubule-associated protein 2) | Millipore | |
| Synaptophysin | Millipore | |
| PSD-95 (postsynaptic density protein-95) | Cell signaling | |
| TrkB (tyrosine kinase receptor B) | Cell signaling | |
| CAMKII ($Ca^{2+}$/calmodulin-dependent protein kinase II)* | Cell signaling | |
| Phosphorylated-CAMKII | Cell signaling | |
| ERK (extracellular signal-regulated kinase)* | Santa Cruz | |
| Phosphorylated-ERK | Santa Cruz | |
| Akt (RAC-alpha serine/threonine-protein kinase)* | Cell signaling | |
| Phosphorylated-Akt | Cell signaling | |
| CREB (cAMP-responsive element-binding protein)* | Cell signaling | |
| Phosphorylated-CREB | Cell signaling | |
| beta-actin* | | |

(in Table above, '*' is reference marker) The results of electrophoresis results obtained from the biomarker proteins and the results of quantification thereof are shown in FIGS. 4 to 19.

As in FIGS. 4 to 19, in most cases of the extract-treated 3×-TG mice ('3×-TG mice+AGE', '3×-TG mice+BKE', and '3×-TG mice+AGE+BKE') 'or' Non-3×-TG mice'), the effect of generating nerve cells similar to that of the control group (extract-untreated 3×-TG mice; indicated as '3×-TG mice') was confirmed. In particular, the group ('3×-TG mice+BKE') treated with *Brassica oleracea* var. *italica* extract (BKE) and the group ('3×-TG mice+AGE+BKE') treated with *Angelica gigas* Nakai extract (AGE) and *Brassica oleracea* var. *italica* extract (BKE) together were observed to have an excellent effect of generating nerve cells. Among them, the effect of generating nerve cells in '3×-TG mice+AGE+BKE' was particularly excellent. These results show that the *Angelica gigas* Nakai extract, the *Brassica oleracea* var. *italica* extract, and the mixed extract of *Angelica gigas* Nakai and *Brassica oleracea* var. *italica* have a neurogenic (regeneration) effect on a neurological injury mouse model (e.g., Alzheimer's disease mouse model). Furthermore, it shows that it has a therapeutic effect on neurodegenerative diseases (e.g., Alzheimer's disease) having nerve damage.

Example 4: Analysis of Active Ingredients According to Extraction Conditions (HPLC)

4.1. Preparation of Test Solution

The *Angelica gigas* Nakai 98% ethanol extract prepared in Example 1.1.1 (extract (1) of Table 2) and the *Angelica gigas* Nakai 90% ethanol extract prepared in Example 1.1.2 (extract (2) in Table 2) were prepared.

For comparison, referring to Example 1.1.1 above, six types of *Angelica gigas* Nakai extracts (extracts (2) to (8) in Table 2) were prepared by varying the types of extraction solvent (ethanol or water) and concentration (30%, 50%, 75%, 80%; w/v) under various temperature conditions.

1 g of the prepared *Angelica gigas* Nakai extract was exactly taken, placed in a 50 ml volumetric flask, and then dissolved by adding about 30 ml methanol (100%), filled with methanol to a marked line, filtered, and used as a sample solution.

4.2. Preparation of Standard Solution 10 mg of decursinol standard product (purity 98% or more), 5 mg of decursinol standard product (purity 98% or more), and 5 mg of decursinol angelate standard product (purity 98% or more) were taken and put in a 25 ml flask, and dissolved by adding 100% methanol, filled with methanol to a marked line, filtered, and used as a sample solution. A standard solution having a concentration of 12.5-25-50-100-200 μg/ml was prepared from this standard solution and used for measuring the calibration curve.

4.3. HPLC Operating Conditions

Testing was performed with the prepared sample solution and standard solution according to the operating conditions of the liquid chromatography below to calculate the content of decursinol, and decursinol angelate:

Column: Cadenza CW C18, (150*4.6 mm, 3 μm) or equivalent column;
Detector: Ultraviolet spectrophotometer (detection wavelength: 330 nm);
Flow rate: 0.7 ml/min;
Mobile phase: Water (A %), Acetonitrile (B %),
0-5 min (20, B), 5-6 min (20→40, B), 6-22 min (40→55, B),
22-23 min (55→80, B), 23-25 min (80, B), 25-27 min (20, B);
Sample injection amount: 10 μl.

4.4. Result

The ingredient analysis results of each of the obtained extracts are shown in Table 2 below.

conventional extract INM-176), 75% (w/v) ethanol extract (extract (5)), and 50% (w/v) ethanol extract (extract (6)). (Extraction temperature of the extract: 40-60° C.). Neuroprotective activity test was performed with reference to the test procedure of Example 2.

The result of CV (cresyl violet acetate) staining of the obtained hippocampal tissue is shown in FIG. 20 below, and the quantitative results of the stained hippocampal tissue is shown in FIG. 21.

As shown in FIGS. 20 and 21, it can be confirmed that 98% ethanol extract (extract (1)) and 90% ethanol extract (extract (2)) has excellent neuroprotective activity as compared with the extracts under conditions outside the concentration range of the extraction solvent,

The invention claimed is:

1. A method for treating neurodegenerative diseases, comprising administrating a mixed extract of *Angelica gigas* Nakai and *Brassica oleracea* var. *italica* to a subject in need thereof,
   wherein the mixed extract of *Angelica gigas* Nakai and *Brassica oleracea* var. italic comprises:
   an extract obtained by extracting *Angelica gigas* Nakai with 90 to 100% (v/v) ethanol at 40 to 60° C., and a *Brassica oleracea* var. italic ethanol extract obtained by extracting *Brassica oleracea* var. *italica* with 20 to 80% (v/v) ethanol at 10 to 80° C.,
   wherein a mixing ratio between *Angelica gigas* Nakai extract and *Brassica oleracea* var. *italica* extract in the mixed extract is 1:1.5 to 10 based on the weight (the weight of *Angelica gigas* Nakai extract: the weight of *Brassica oleracea* var. *italica* extract).

2. The method for treating neurodegenerative diseases according to claim 1, wherein the *Brassica oleracea* var. *italica* ethanol extract is extracted under conditions of pH 7 to 9.

TABLE 2

| | | (1) | (2) | (3) | (4) | (5) | (6) | (7) | (8) |
|---|---|---|---|---|---|---|---|---|---|
| Extraction solvent | | 98% Ethanol | 90% Ethanol | 98% Ethanol | 80% Ethanol | 75% Ethanol | 50% Ethanol | 30% Ethanol | Water (hot water) |
| Extraction temperature | | 40~60° C. | | 90° C. | | 40~60° C. | | | — |
| Total extracted compounds from 100 g dried *Angelica gigas* Nakai (mg) | Decursin | 3243 | 2911 | 1640 | 2351 | 2089 | 1560 | 1101 | 19 |
| | Decursinol angelate | 1995 | 1724 | 790 | 1477 | 1327 | 1116 | 865 | 10 |
| | Nodakenin | 2982 | 2562 | 1332 | 2318 | 1913 | 1571 | 543 | 559 |
| | β-Sitosterol | 324 | 269 | 85 | 212 | 145 | 88 | 35 | 13 |

As shown in Table 1 above, it can be confirmed that the ethanol extract of *Angelica gigas* Nakai of Examples 1.1.1 and 1.1.2 is remarkably higher in the content of useful compounds in the extract as compared with other extracts having different extraction conditions (extraction solvent concentration, type, extraction temperature, etc.).

Example 5: Neuroprotective Activity Test According to the Concentration of Extraction Solvent (Ethanol)

Among the *Angelica gigas* Nakai extracts obtained under various extraction conditions prepared in Example 4, the neuroprotective activity test was performed on 98% (w/v) ethanol extract (extract (1); Example 1.1.1 extract) and 90% (w/v) ethanol extract (extract (2); Example 1.1.2 extract), and 80% (w/v) ethanol extract (extract (4); equivalent to a 3. The method for treating neurodegenerative diseases according to claim 1, wherein the neurodegenerative disease is dementia, Parkinson's disease (PD), Huntington's disease, or amyotrophic lateral sclerosis.

4. The method for treating neurodegenerative diseases according to claim 3, wherein the dementia is Alzheimer's disease.

5. A method for protecting nerve cells or regenerating nerve cells, comprising administrating a mixed extract of *Angelica gigas* Nakai and *Brassica oleracea* var. *italica* to a subject in need of the protection of nerve cells or the regeneration of nerve cells, wherein the mixed extract of *Angelica gigas* Nakai and *Brassica oleracea* var. italic comprises:
   an *Angelica gigas* Nakai ethanol extract obtained by extracting *Angelica gigas* Nakai with 90 to 100% (v/v) ethanol at 40 to 60° C., and a *Brassica oleracea* var.

italic ethanol extract obtained by extracting *Brassica oleracea* var. *italica* with 20 to 80% (v/v) ethanol at 10 to 80° C., wherein a mixing ratio between *Angelica gigas* Nakai extract and *Brassica oleracea* var. *italica* extract in the mixed extract is 1:1.5 to 10 based on the weight (the weight of *Angelica gigas* Nakai extract: the weight of *Brassica oleracea* var. *italica* extract).

\* \* \* \* \*